United States Patent
Chang et al.

(10) Patent No.: US 10,584,154 B2
(45) Date of Patent: Mar. 10, 2020

(54) VESICLES COMPRISING LECTINS EXPRESSED ON THE SURFACE AND METHODS OF USE THEREOF TO DELIVER AN AGENT TO AUTOPHAGIC AND APOPTOTIC CELLS

(71) Applicant: TZU CHI UNIVERSITY, Hualien (TW)

(72) Inventors: Hsin-Hou Chang, Hualien (TW); Der-Shan Sun, Hualien (TW)

(73) Assignee: TZU CHI UNIVERSITY, Hualien (TW)

( * ) Notice: Subject to any disclaimer, the term of this patent is extended or adjusted under 35 U.S.C. 154(b) by 0 days.

(21) Appl. No.: 15/855,742

(22) Filed: Dec. 27, 2017

(65) Prior Publication Data

US 2019/0194281 A1   Jun. 27, 2019

(51) Int. Cl.
| | | |
|---|---|---|
| *A61K 31/407* | (2006.01) | |
| *A61K 31/704* | (2006.01) | |
| *A61K 31/713* | (2006.01) | |
| *A61K 33/24* | (2019.01) | |
| *A61K 47/62* | (2017.01) | |
| *A61K 47/69* | (2017.01) | |
| *C07K 14/47* | (2006.01) | |
| *C07K 14/705* | (2006.01) | |
| *C07K 17/02* | (2006.01) | |

(52) U.S. Cl.
CPC ........ *C07K 14/4726* (2013.01); *A61K 31/407* (2013.01); *A61K 31/704* (2013.01); *A61K 31/713* (2013.01); *A61K 33/24* (2013.01); *A61K 47/62* (2017.08); *A61K 47/6909* (2017.08); *A61K 47/6911* (2017.08); *C07K 14/70546* (2013.01); *C07K 14/70596* (2013.01); *C07K 17/02* (2013.01); *C07K 2319/01* (2013.01); *C07K 2319/33* (2013.01)

(58) Field of Classification Search
CPC .......... C07K 14/4726; C07K 14/70546; C07K 14/70596; C07K 17/02; C07K 2319/01; C07K 2319/33; A61K 47/6909
See application file for complete search history.

(56) References Cited

U.S. PATENT DOCUMENTS

2010/0151573 A1   6/2010   King
2012/0148668 A1   6/2012   Consigny et al.

OTHER PUBLICATIONS

Yamazaki N, et al. (1994) Methods in Enzymology. 242:56-65. (https://doi.org/10.1016/0076-6879(94)42008-4).*
Sharma A, et al. (2004) Journal of Antimicrobial Chemotherapy. 54:761-766. (https://doi.org/10.1093/jac/dkh411).*
Bogdanov AA, et al. (Apr. 1988) FEBS Letters. 231(2):381-384.*
Office Action and Search Report dated Oct. 9, 2018 from corresponding Taiwan application 106146090, 7 pages.
Minnelli, Cristina, et al. "Selective induction of apoptosis in MCF7 cancer-cell by targeted liposomes functionalised with mannose-6-phosphate." J Drug Target. Mar. 2018;26(3):242-251. doi: 10.1080 1061186X.2017.1365873. Epub Aug. 25, 2017.J Drug Target. Mar. 2018;26(3):242-251. doi: 10.1080, Abstract.
G. A. Van Tilborg et al: "AnnexinV-functionaized multimodal liposomes as contrast agents for apoptotic cells", International Society for Magnetic Resonance in Medicine, vol. 13, 2005, p. 2596
Yung-Chih Kuo et al: "Rescuing apoptotic neurons in Alzheimer's disease using wheat germ agglutinin-conjugated and cardiolipin-conjugated liposomes with encapsulated nerve growth factor and curcumin", International Journal of Nanomedicine, May 1, 2015 (May 1, 2015), pp. 2653-2672.
Jeong, D. et al., Nanovesicles Engineered From ES Cells for Enhanced Cell Proliferation. Biomaterials. 2014; 35(34): 9302-9310.
Yu, Bo et al., Microfluidic Methods for Production of Liposomes, Methods Enzymol. 2009; 465: 129-141.

* cited by examiner

*Primary Examiner* — Robert S Landsman
(74) *Attorney, Agent, or Firm* — Duane Morris LLP

(57) ABSTRACT

The invention creates engineered surface protein expression on vesicles for specific targeting and delivery of agents to autophagic and apoptotic cells. Moreover, the vesicles of the invention can achieve a synergistic effect on the targeting and drug delivery to autophagic and apoptotic cells and autophagic and apoptotic cells-containing tissues.

20 Claims, 27 Drawing Sheets
(21 of 27 Drawing Sheet(s) Filed in Color)

Single test (S-8) (Lipo vs Apo)

(a)

(b)

MP-drug transfer to F10-mice

VESICLES COMPRISING LECTINS EXPRESSED ON THE SURFACE AND METHODS OF USE THEREOF TO DELIVER AN AGENT TO AUTOPHAGIC AND APOPTOTIC CELLS

FIELD OF THE INVENTION

The present invention is related to the field of delivery of an agent to cells. Particularly, the present invention is related to the delivery of an agent to autophagic and/or apoptotic cells and tissues through a vesicle with an engineered protein expressed on or conjugated to the surface thereof.

BACKGROUND OF THE INVENTION

Apoptosis is a well-studied pathway of programmed cell death. Non-apoptotic forms of cell elimination include those with features of necrosis and autophagy. Apoptosis plays a crucial role in developing and maintaining the health of the body by eliminating old cells, unnecessary cells, and unhealthy cells. Too little or too much apoptosis can play a role in many diseases. When apoptosis does not work correctly, cells that should be eliminated may persist and become immortal for example, in cancer and leukemia. When apoptosis works overly well, it kills too many cells and inflicts grave tissue damage. This is the case in strokes and neurodegenerative disorders such as Alzheimer's, Huntington's, and Parkinson's diseases.

Autophagy, the process by which proteins and organelles are sequestered in double-membrane structures called autophagosomes and delivered to lysosomes for degradation, is critical in diseases. In addition to cancer and neurodegeneration, modulation of autophagy is a therapeutic strategy in a wide variety of additional diseases and disorders. For example, several liver diseases, cardiac diseases and muscle diseases are correlated with the accumulation of misfolded protein aggregates. In such diseases, agents that increase cellular autophagy may enhance the clearance of disease-causing aggregates and thereby contribute to treatment and reduce disease severity. Moreover, inhibitors of autophagy may function as therapeutic agents in the treatment of pancreatitis.

Therefore, there is a need to develop a means of modulating apoptosis and autophagy in cells thereby curing or ameliorating autophagy-associated diseases.

SUMMARY OF THE INVENTION

The invention provides a protein-conjugated vesicle, comprising one or more lectins or a fragment thereof expressed or conjugated to the surface of the vesicle and optionally an agent.

In one embodiment, the agent is encapsulated within the vesicle or attach to outer surface of the vesicle. Particular embodiments of the vesicle include liposome and micelle. The vesicle can be artificially engineered or cell-derived.

Particular embodiments of the lectin or a fragment include, but are not limited to, cation-dependent mannose-6-phosphate receptor (M6PR), P-selectin, E-selectin, L-selectin, P-selectin-ligand-1 (PSGL-1), CD22, CD206, galectin 3, annexin V, CD31, integrin αLβ2, VE-cadherin, CD44, CD300a, CD47, thrombospondin 1 (TSP1) and CD36, which are used as the first protein.

Particular embodiments of the lectin or a fragment include, but are not limited to, CD300a, CD47, thrombospondin 1 (TSP1) and CD36, Toll like receptor 4 (TLR4) or a fragment thereof, which are used as the second protein.

Particular embodiments of the lectin or a fragment include, but are not limited to, one or more the first protein and one or more the second proteins.

In some embodiments, the vesicle comprises M6PR in combination with P-selectin, E-selectin, PSGL-1 or galectin 3. In some embodiments, the vesicle comprises Siglec 2 in combination with P-selectin, galectin 3 or CD31.

In some embodiments, the vesicle comprises P-selectin or M6PR in combination with TLR4, galectin 3, CLEC2, Integrin αLβ2 or CD31.

Particular embodiments of the agent include, but are not limited to, diagnostic contrast agent, a cell survival enhancing agent, a cell survival suppressing agent, a cell component, an organelle, a cell, a cytotoxic agent, an antitumor drug, a toxin or an antibody a lipid, a protein, DNA, RNA, a therapeutic agent or a nanomaterial.

The invention also provides a pharmaceutical composition comprising a vesicle of the invention and a pharmaceutically acceptable carrier.

The invention also provides a method for targeting delivery of an agent to an autophagic and/or apoptotic cell and a tissue containing the cell, comprising administering a protein-conjugated vesicle of the invention to a subject.

BRIEF DESCRIPTION OF THE DRAWING

The patent or application file contains at least one drawing executed in color. Copies of this patent or patent application publication with color drawing(s) will be provided by the Office upon request and payment of the necessary fee.

The relative fluorescent intensity of mouse organs, which include heart, lung, liver and spleen, with or without TAA and liposome treatments were measured. A, a bright-field image indicated mouse organs, which include heart, lung, liver and spleen. B-S, fluorescent images, in which the red parts in pseudo color images B, D, F, H, J, are showed in C, E, G, I, K. Synergistic targeting: B-C, M6PR plus P-selectin; D-E M6PR plus galectin 3 and Siglec 2; F-G, M6PR plus MMR and integrin αLβ2; H-I, M6PR plus CD31 and annexin V; J-K, M6PR plus CD44 and VE-cadherin. All protein conjugated liposomes showed higher liver preferential targeting properties compared to the control groups treated with unconjugated liposomes (vehicle). In addition, the fluorescent levels are higher in those groups with two protein conjugation as compared to the single protein conjugated groups.

Figure 8:
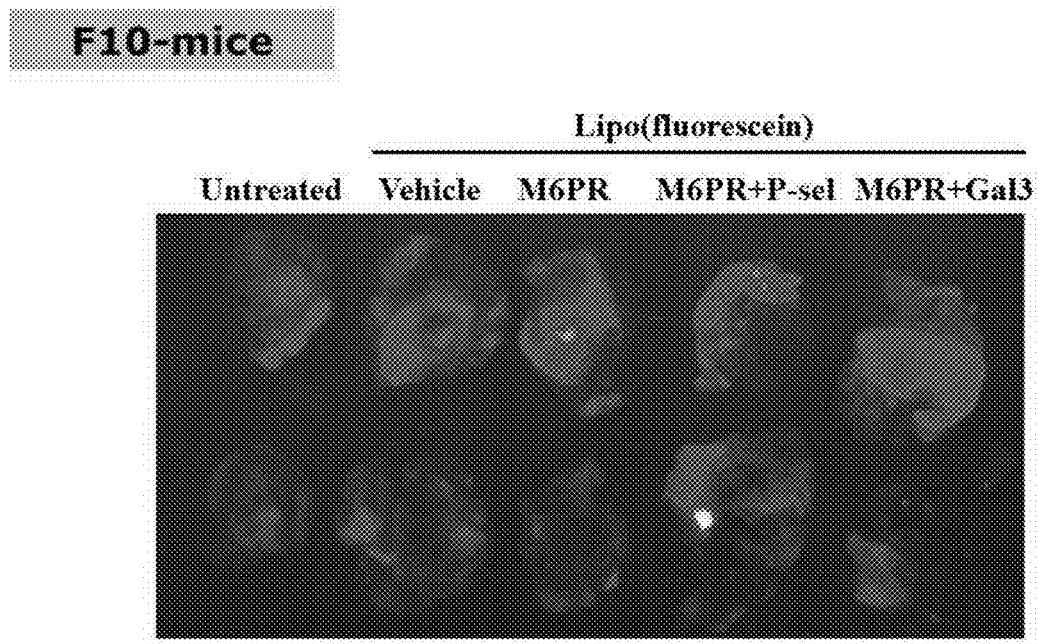

FIG. 8 shows that an in vivo image system (IVIS) is used to identify whether recombinant protein-conjugated fluorescent liposome has targeting effect on tumors. We found that fluorescence loaded liposomes are more efficiently targeting to B16-F10 melanoma cell formed tumors (M6PR, M6PR+P-selectin and M6PR+galectin3 groups vs. untreated and vehicle groups).

Figure 9:
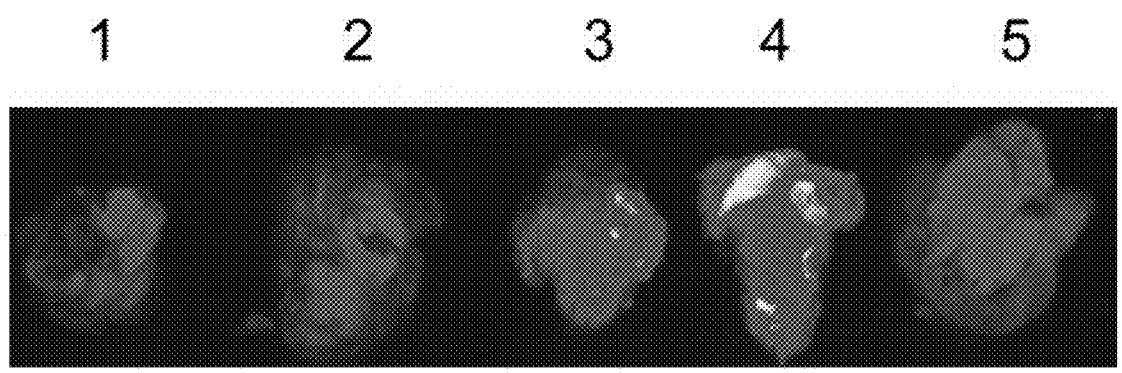

FIG. 9 shows an in vivo image system (IVIS) was used to identify whether recombinant protein-conjugated fluorescent liposome has targeting effect on injured white adipose tissues (pretreated with anti-fat-tissue antibodies). C57B1/6J mice were treated with or without rabbit anti-mouse fat cell antibodies. The mice were then treated with fluorescent (calcein red) liposomes with recombinant protein conjugations. Groups: 1, untreated; 2, unconjugated liposomes; 3, M6PR+galectin3; 4, M6PR+P-selectin; 5, M6PR.

Figure 10:
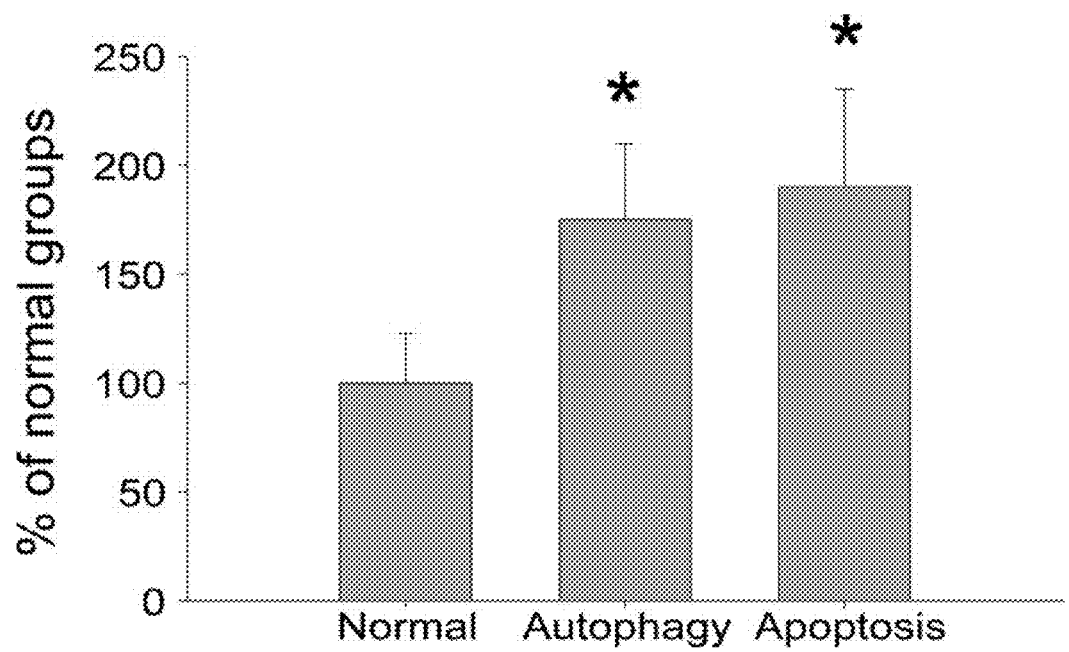

FIG. 10 shows the injured mouse liver contains autophagic and apoptotic cells. *$P<0.05$, compared to normal groups. (n=4).

Figure 11:
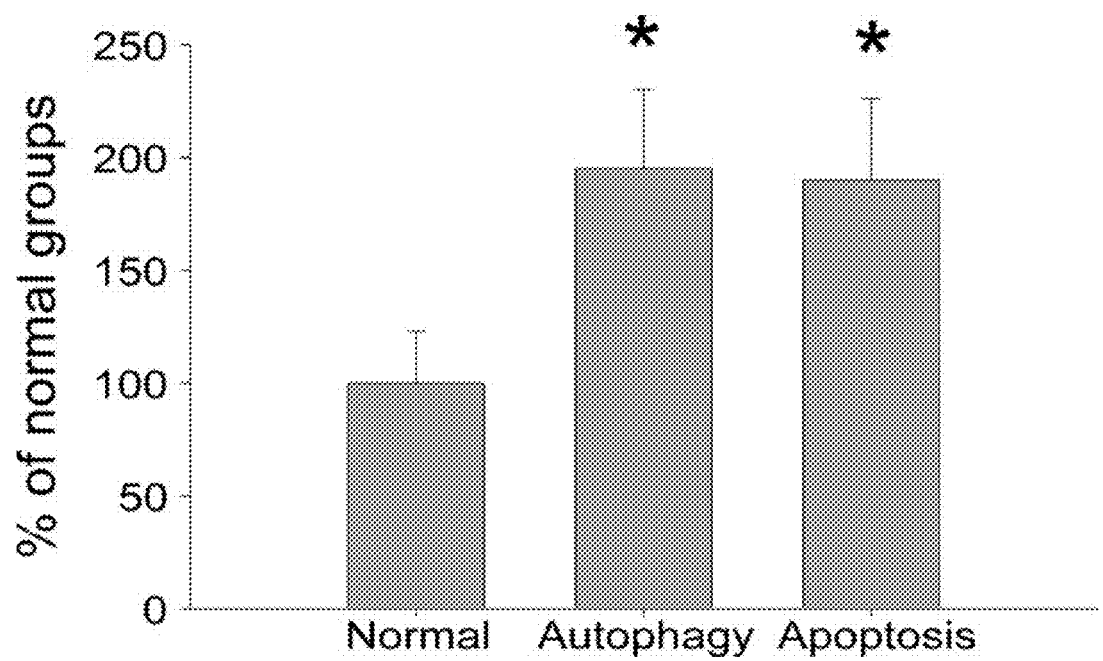

FIG. 11 shows that the mouse B16-F10 cell-formed solid tumors contain autophagic and apoptotic cells. *$P<0.05$, compared to normal groups. (n=4).

Figure 12:
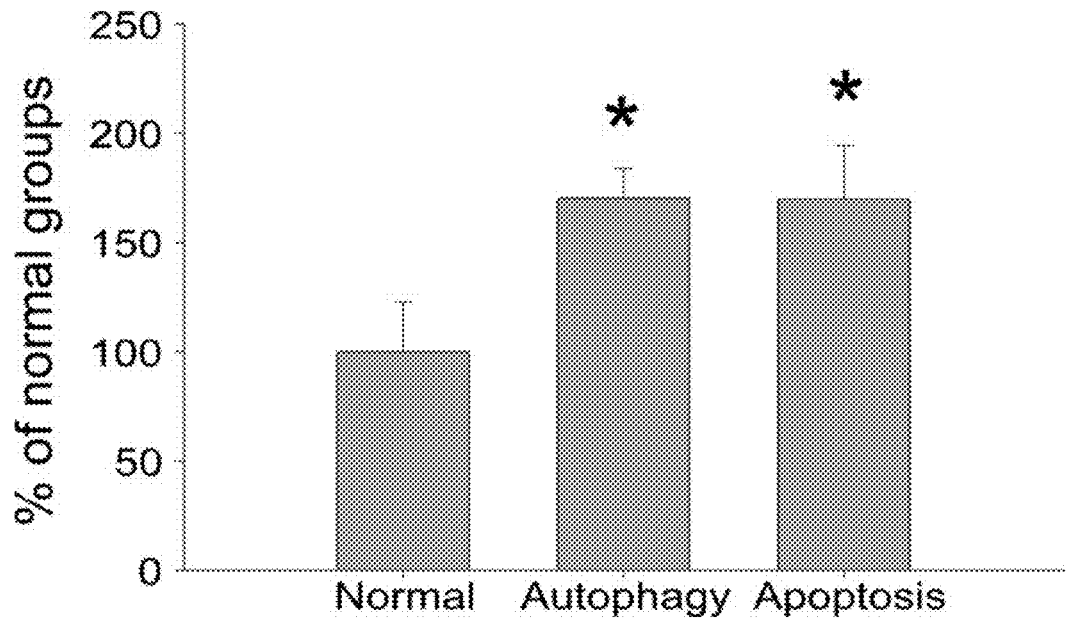

FIG. 12 shows the anti-fat antibody treated mouse adipose tissue contains autophagic and apoptotic cells. *$P<0.05$, compared to normal groups. (n=4).

Figure 13:
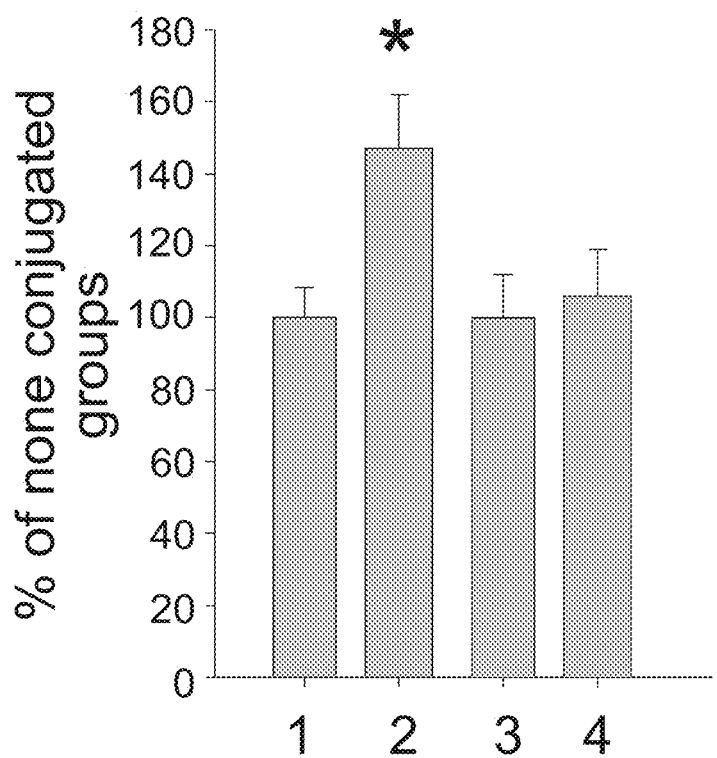

FIG. 13 shows blocking of liposomes target to apoptotic cells. Blocking antibody and soluble M6PR recombinant protein (panels 3 and 4, respectively) are able to block the targeting of M6PR-conjugated liposomes/microvesicles (panel 2) targeting to the apoptotic cells and may serve as the antidotes. Liposome preparations: panel 1, unconjugated; panel 2, M6PR+P-selectin-conjugated; 3, M6PR+P-selectin-conjugated liposomes+blocking antibody; 4, M6PR+P-selectin-conjugated liposomes+soluble M6PR recombinant protein.

Figure 14:
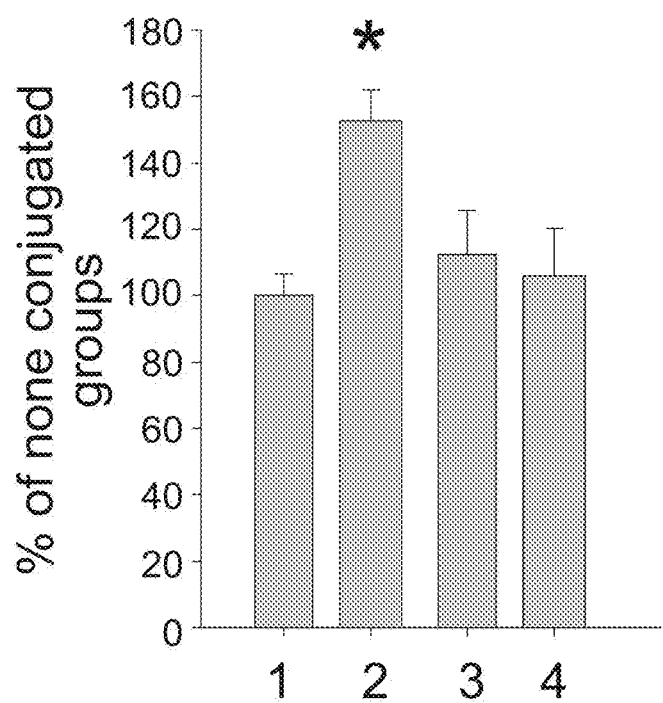

FIG. 14 shows blocking of liposomes target to autophagy cells. Blocking antibody and soluble M6PR recombinant protein (panels 3 and 4, respectively) are able to block the targeting of M6PR+P-selectin-conjugated liposomes/microvesicles (panel 2) targeting to the autophagy cells and may serve as the antidotes. Liposome preparations: panel 1, unconjugated; panel 2, M6PR+P-selectin-conjugated; 3, M6PR+P-selectin-conjugated liposomes+blocking antibody; 4, M6PR+P-selectin-conjugated liposomes+soluble M6PR recombinant protein.

Figure 15:
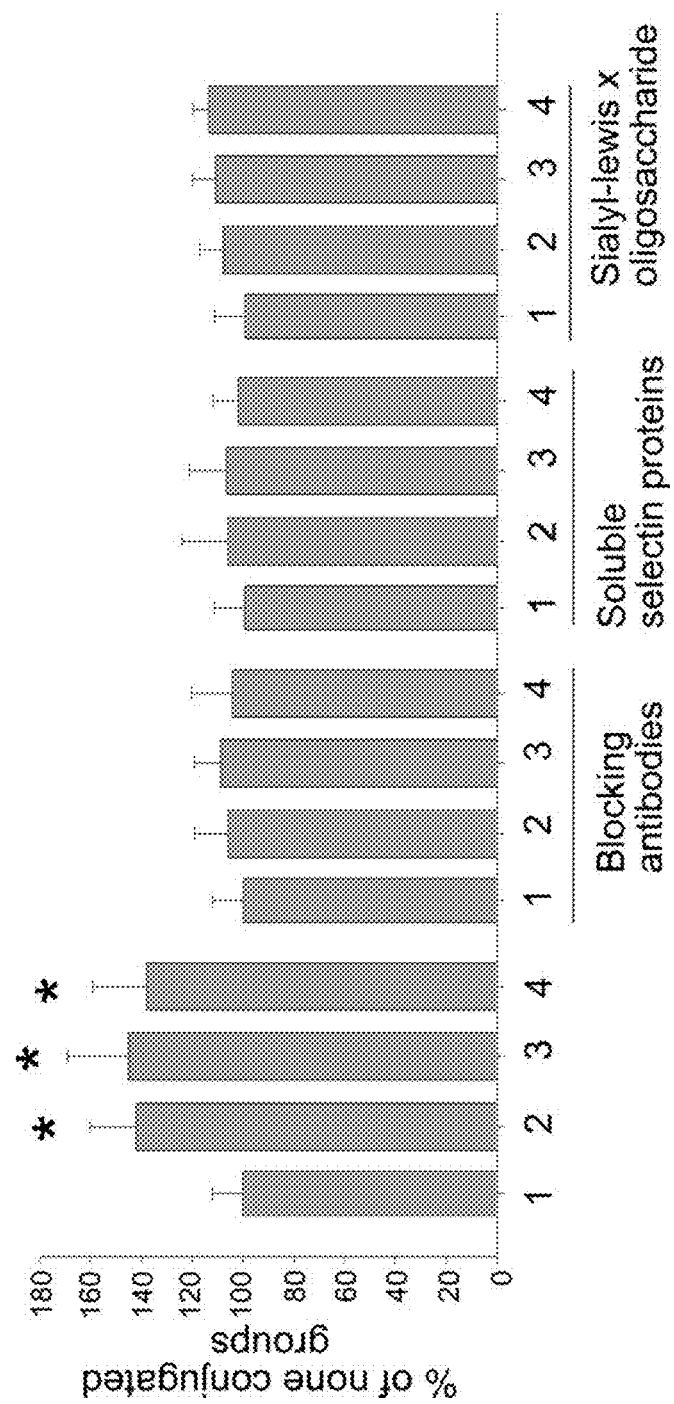

FIG. 15 shows liposome targeting to apoptotic cells. Groups 1-4 are indicated untreated, M6PR+P-selectin, M6PR+E-selectin and M6PR+PSGL-1-conjugated groups respectively. *$P<0.05$, compared to untreated (panel 1) groups. (n=4). These results suggested that the specific blocking antibodies, specific soluble recombinant proteins and sialyl-lewis x oligosaccharide are able to serve as the antidotes to block P-selectin, E-selectin and PSGL-1-conjugated liposomes targeting to apoptotic cells.

Figure 16:
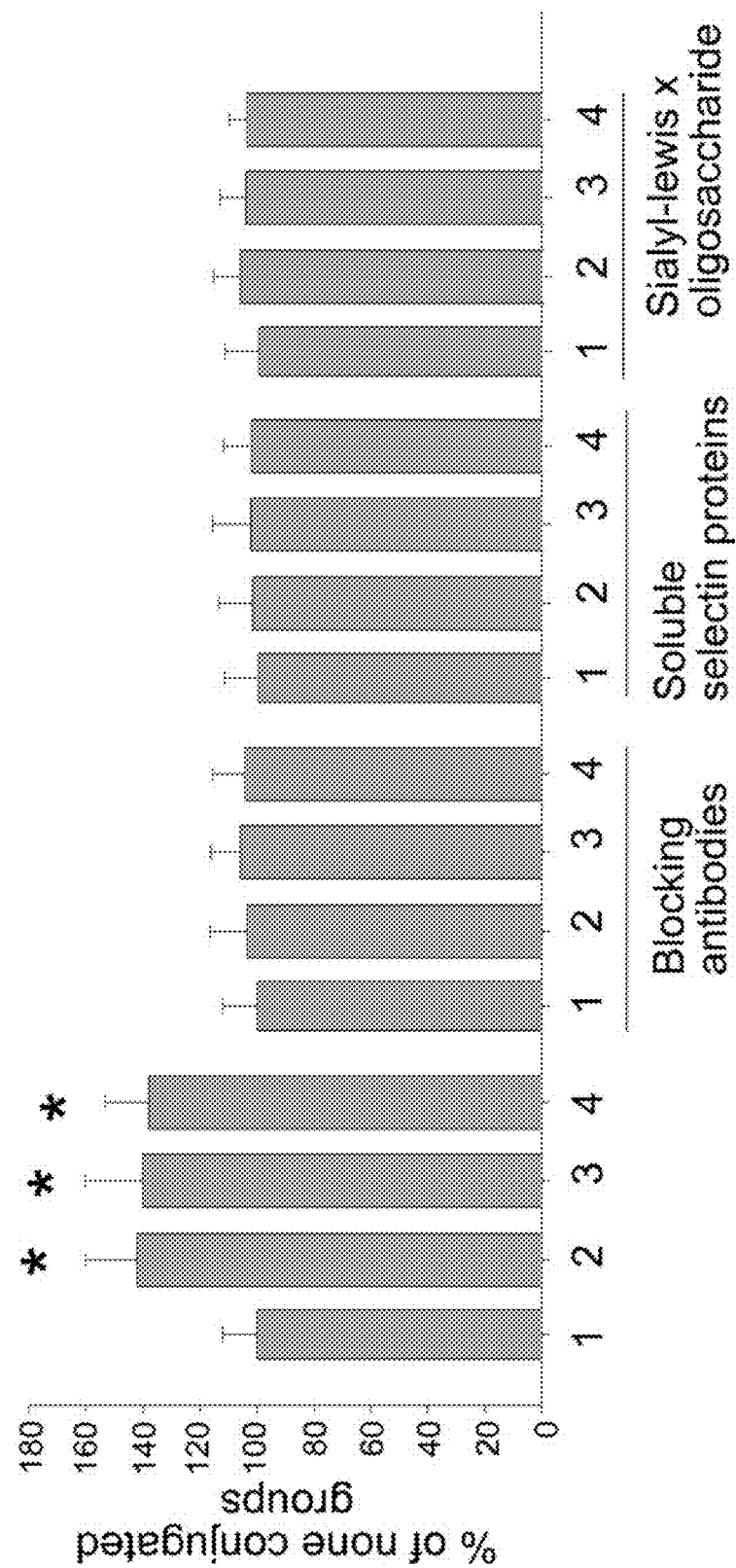

FIG. 16 shows liposome targeting to autophagy cells. Groups 1-4 are indicated untreated, M6PR+P-selectin, M6PR+E-selectin and M6PR+PSGL-1-conjugated groups respectively. *$P<0.05$, compared to untreated (panel 1) groups. (n=4). These results suggested that the specific blocking antibodies, specific soluble recombinant proteins and sialyl-lewis x oligosaccharide are able to serve as the antidotes to block P-selectin, E-selectin and PSGL-1-conjugated liposomes targeting to autophagy cells.

Figure 17:
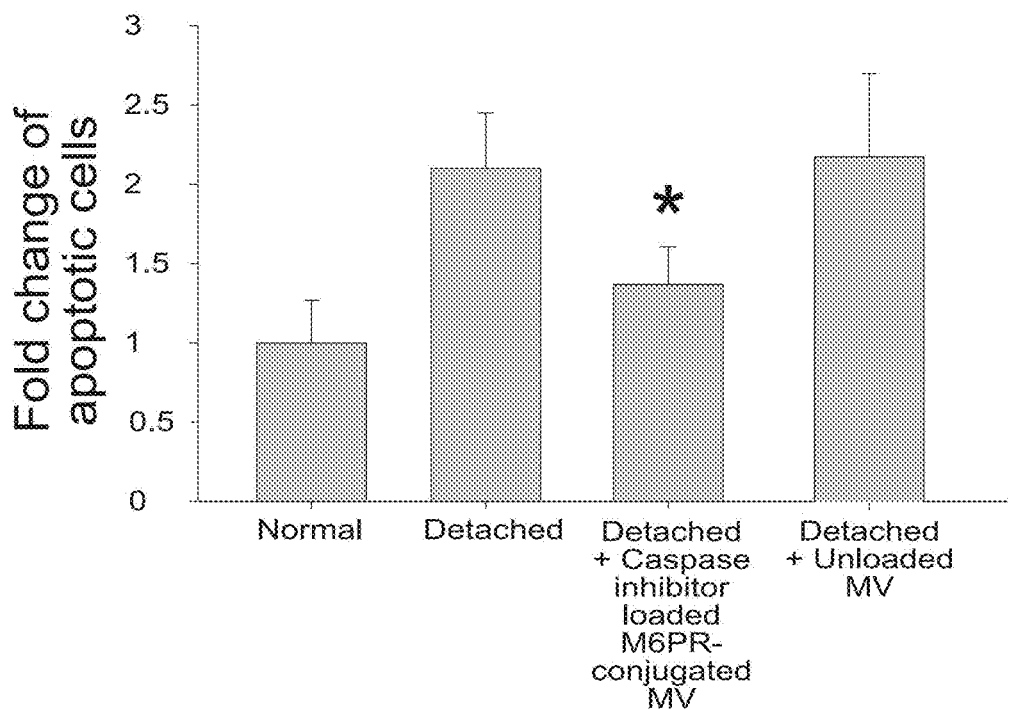

FIG. 17 shows caspase-3 inhibitor-loaded M6PR-conjugated liposomes on the rescue of detached apoptotic B16-F10 cells in vitro. *$P<0.05$, compared to detached groups. (n=4). These results suggested that the M6PR-conjugated liposomes can specific deliver liposome-loaded caspase-3 inhibitor (BioVision) into apoptotic cells.

Figure 18:
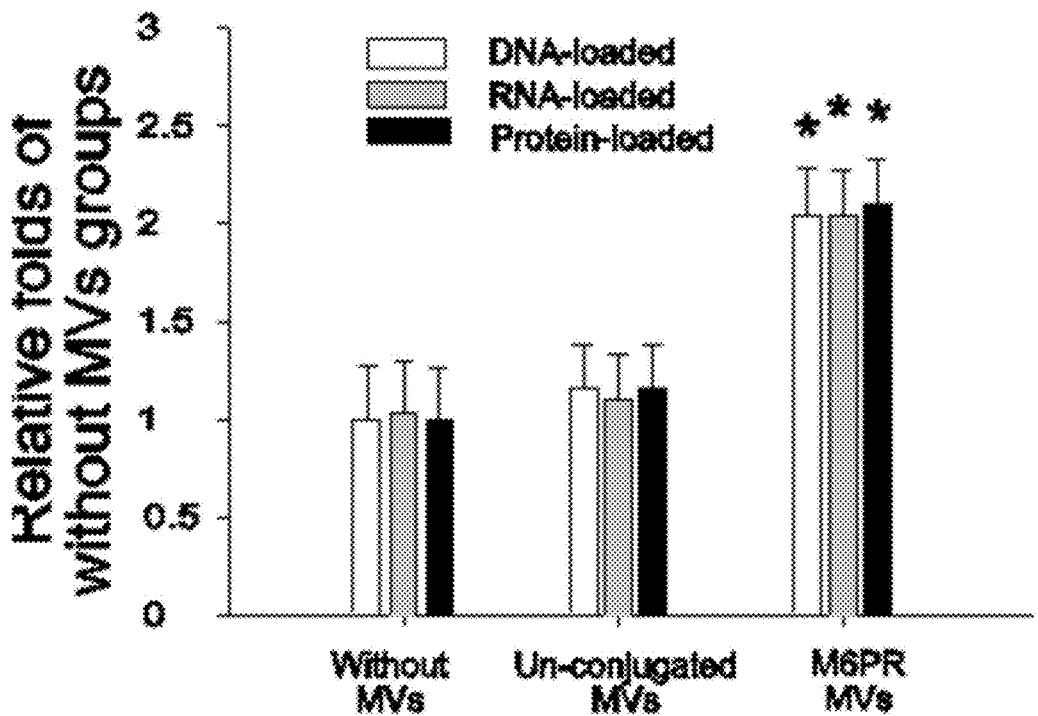

FIG. 18 shows DNA-(white panels), RNA-(gray panels), protein (blacked panels)-loaded and M6PR-conjugated liposmoes on the delivery of DNA, RNA and protein to B16-F10 cells. The relative fluorescence levels of B16-F10 cells with or without liposomes were analyzed using flow cytometry. *$P<0.05$, compared to respective unconjugated groups. (n=4).

Figure 19:
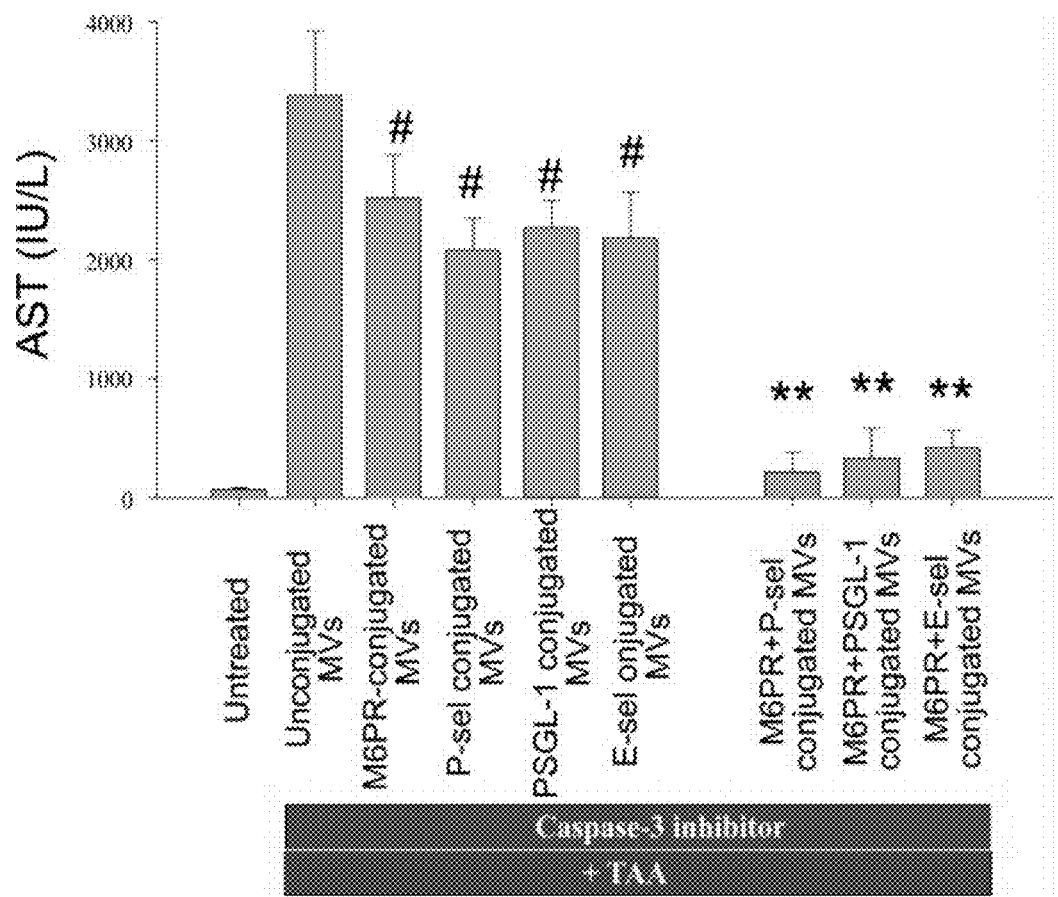

FIG. 19 shows M6PR, M6PR+P-selectin-, M6PR+E-selectin- and M6PR+PSGL-1-conjugated, caspase-3 inhibitor-loaded liposomes/MVs on the rescue of TAA treated mice. The plasma aspartate transaminase (AST) levels were analyzed. P-selectin: P-sel; E-selectin: E-sel; P-selectin glycoprotein ligand 1: PSGL-1°#$P<0.05$, compared to unconjugated MVs groups. **$P<0.01$, compared to respective recombinant protein conjugated groups. (n=6).

Figure 20:
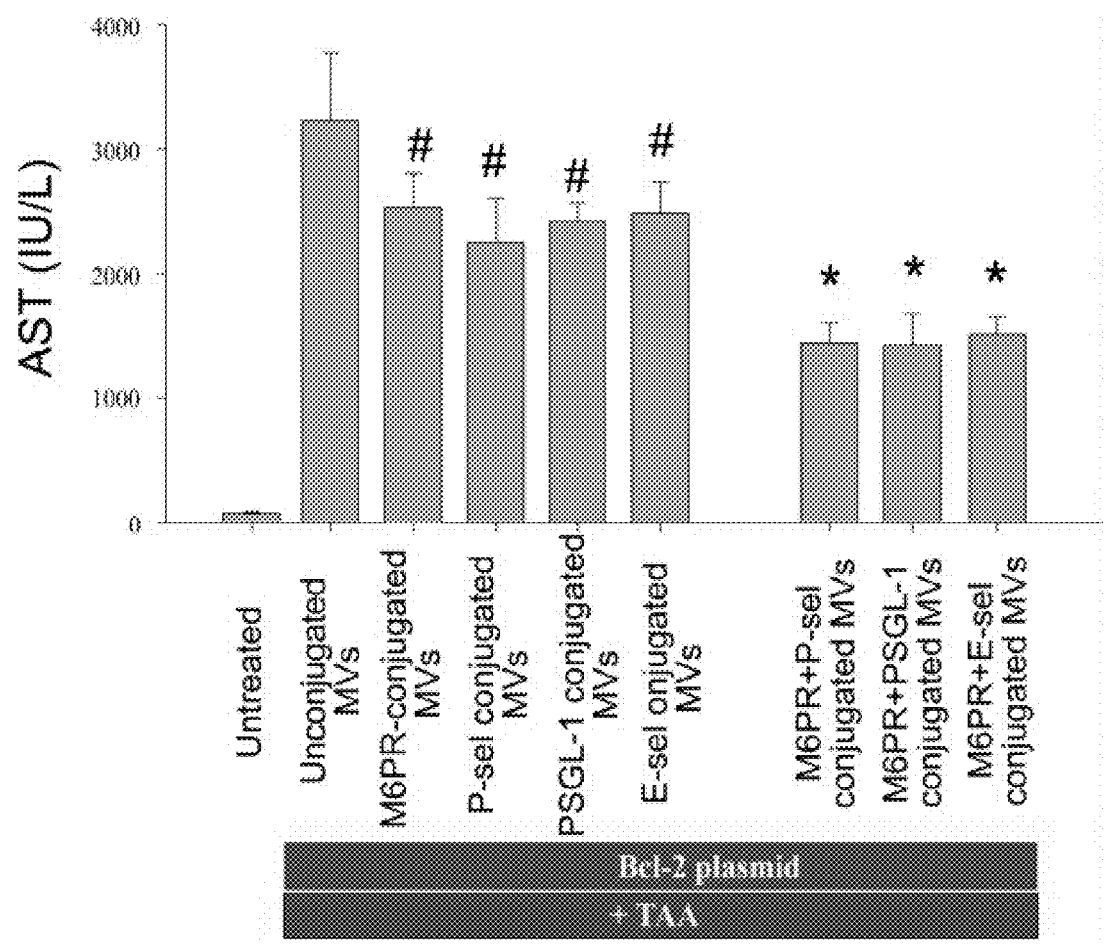

FIG. 20 shows M6PR, M6PR+P-selectin-, M6PR+E-selectin- and M6PR+PSGL-1-conjugated, Bcl-2 expression plasmid-loaded liposomes/MVs on the rescue of TAA treated mice. The plasma aspartate transaminase (AST) levels were analyzed. P-selectin: P-sel; E-selectin: E-sel; P-selectin glycoprotein ligand 1: PSGL-1°#$P<0.05$, compared to without Liposomes/MVs groups. **$P<0.01$, compared to respective recombinant protein conjugated groups. (n=6).

Figure 21:
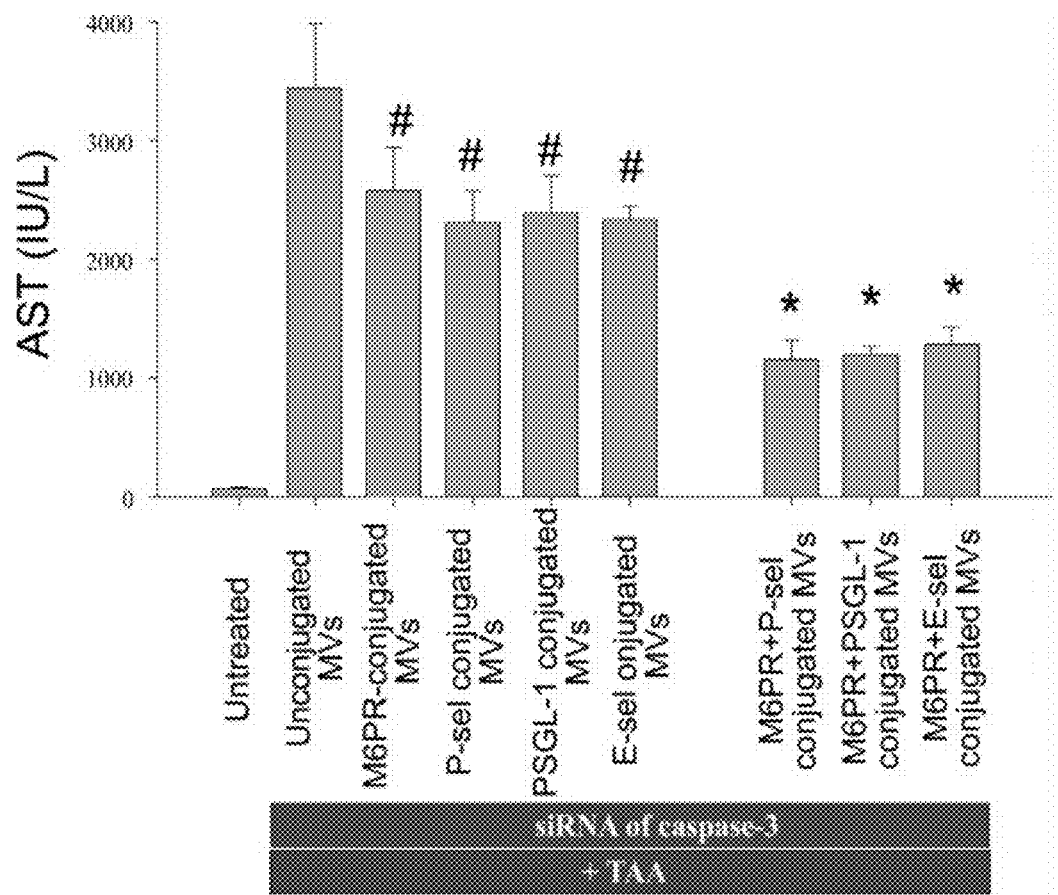

FIG. 21 shows M6PR, M6PR+P-selectin-, M6PR+E-selectin- and M6PR+PSGL-1-conjugated, caspase-3 siRNA-loaded liposomes/MVs on the rescue of TAA treated mice. The plasma aspartate transaminase (AST) levels were analyzed. P-selectin: P-sel; E-selectin: E-sel; P-selectin glycoprotein ligand 1: PSGL-1°#$P<0.05$, compared to unconjugated MVs groups. **$P<0.01$, compared to respective recombinant protein conjugated groups. (n=6).

Figure 22:
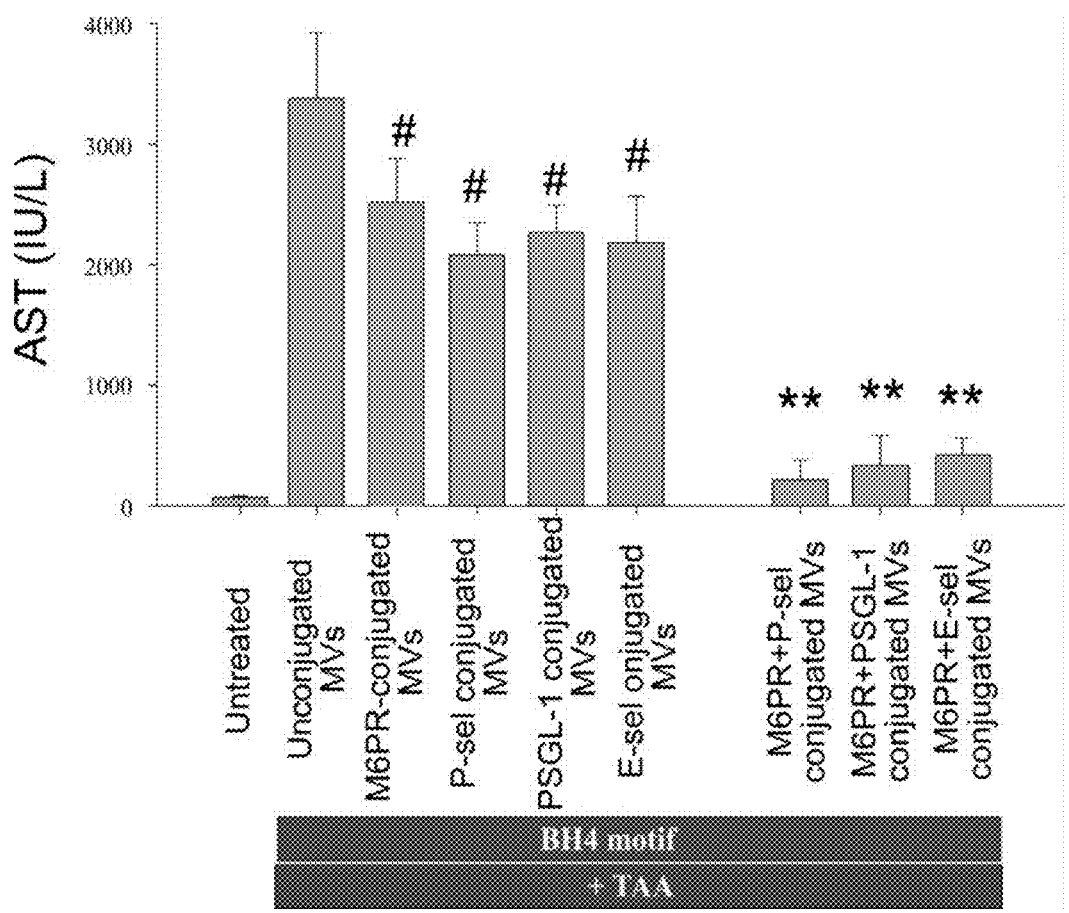

FIG. 22 shows M6PR, M6PR+P-selectin-, M6PR+E-selectin- and M6PR+PSGL-1-conjugated antiapoptotic Bcl-xL-derived BH4 motif loaded liposomes/MVs on the rescue of TAA treated mice. The plasma aspartate transaminase (AST) levels were analyzed. P-selectin: P-sel; E-selectin: E-sel; P-selectin glycoprotein ligand 1: PSGL-1°#$P<0.05$, compared to unconjugated MVs groups. **$P<0.01$, compared to respective recombinant protein conjugated groups (loaded with antiapoptotic Bcl-xL-derived BH4 motif). (n=6).

Figure 23:
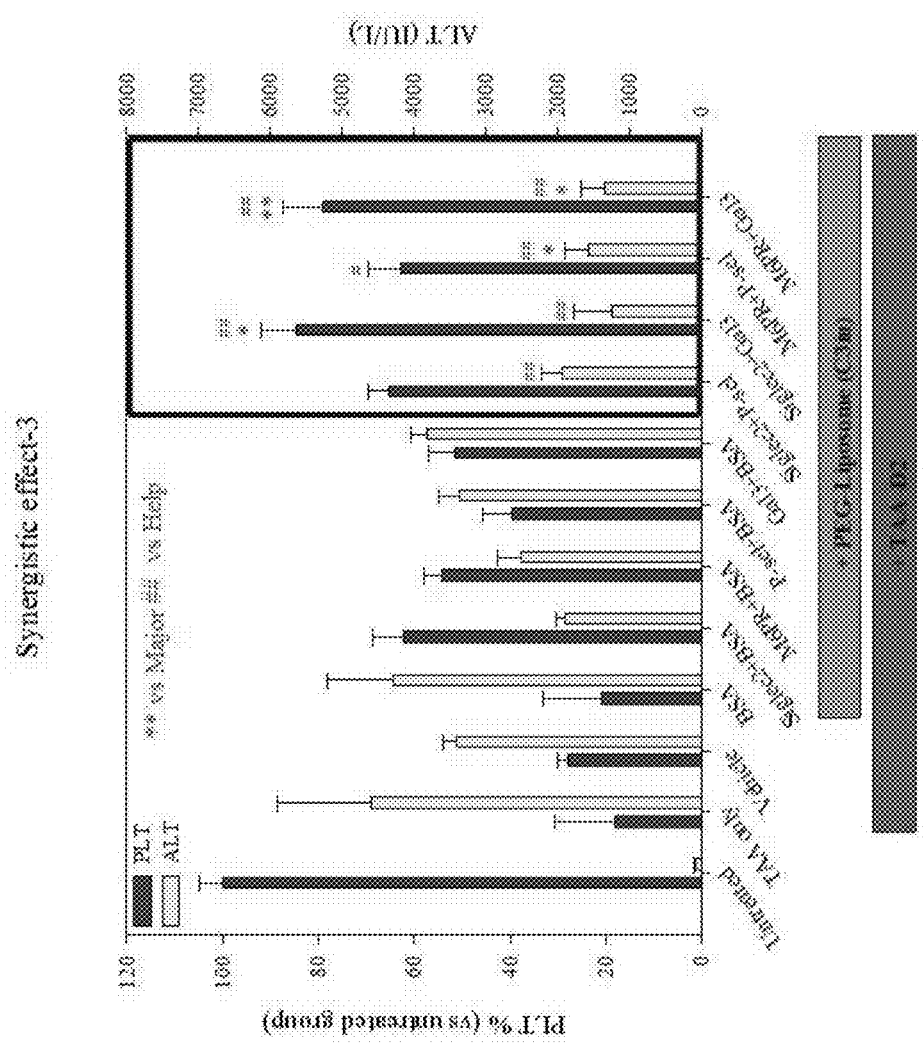

FIG. 23 shows synergistic effect of M6PR+galectin 3, M6PR+P-selectin, Siglec 2+P-selectin and Siglec 2+galectin 3-conjugated caspase 3 inhibitor-loaded liposomes/MVs on the rescue of TAA treated mice. The platelet count (PLT) and plasma alanine aminotransferase (ALT) levels were analyzed. P-selectin: P-sel; galectin 3: Gal3. ##$P<0.01$, compared to without BSA groups. *$P<0.05$, **$P<0.01$, compared to respective single recombinant protein conjugated groups (loaded with caspase 3 inhibitor) (n=6).

Figure 24:
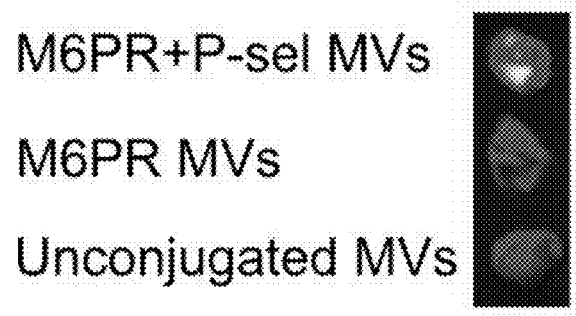

FIG. 24 shows IVIS analysis of M6PR and P-selectin (P-sel) conjugated liposome/MV on the facilitation of fluorescence-labeled CD34+ stem cells targeting to injury tissues. Here showed the liver in TAA-treated mouse model.

Figure 25:
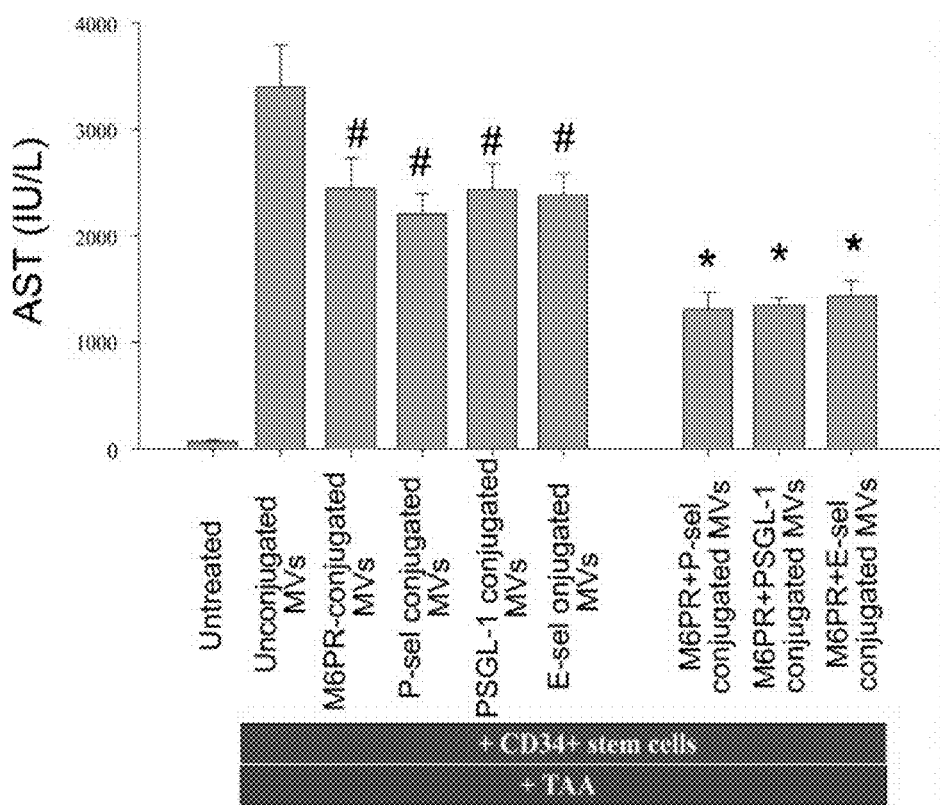

FIG. 25 shows M6PR, M6PR+P-selectin-, M6PR+E-selectin- and M6PR+PSGL-1-conjugated liposomes/MVs on the rescue of TAA treated mice. The plasma aspartate transaminase (AST) levels were analyzed. P-selectin: P-sel; E-selectin: E-sel; P-selectin glycoprotein ligand 1: PSGL-1. # $P<0.05$, compared to unconjugated MVs groups. **$P<0.01$, compared to respective M6PR-conjugated Liposomes/MVs groups. (n=6).

Figure 26:
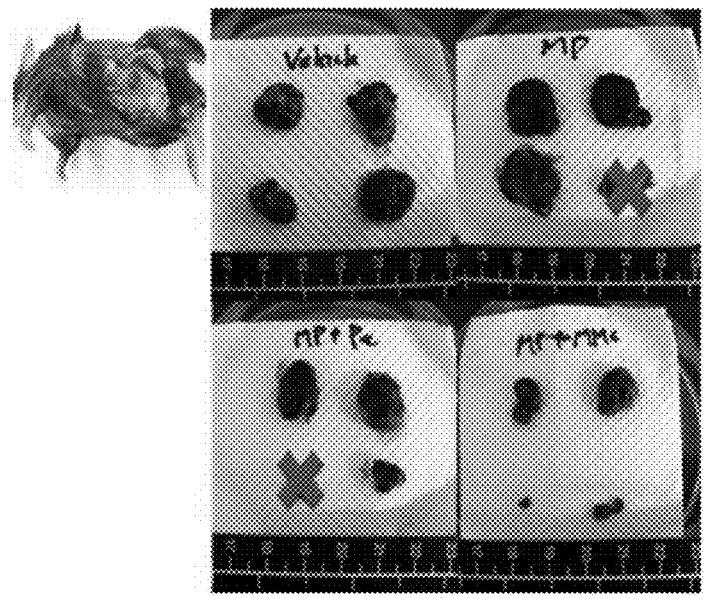
Figure 26:
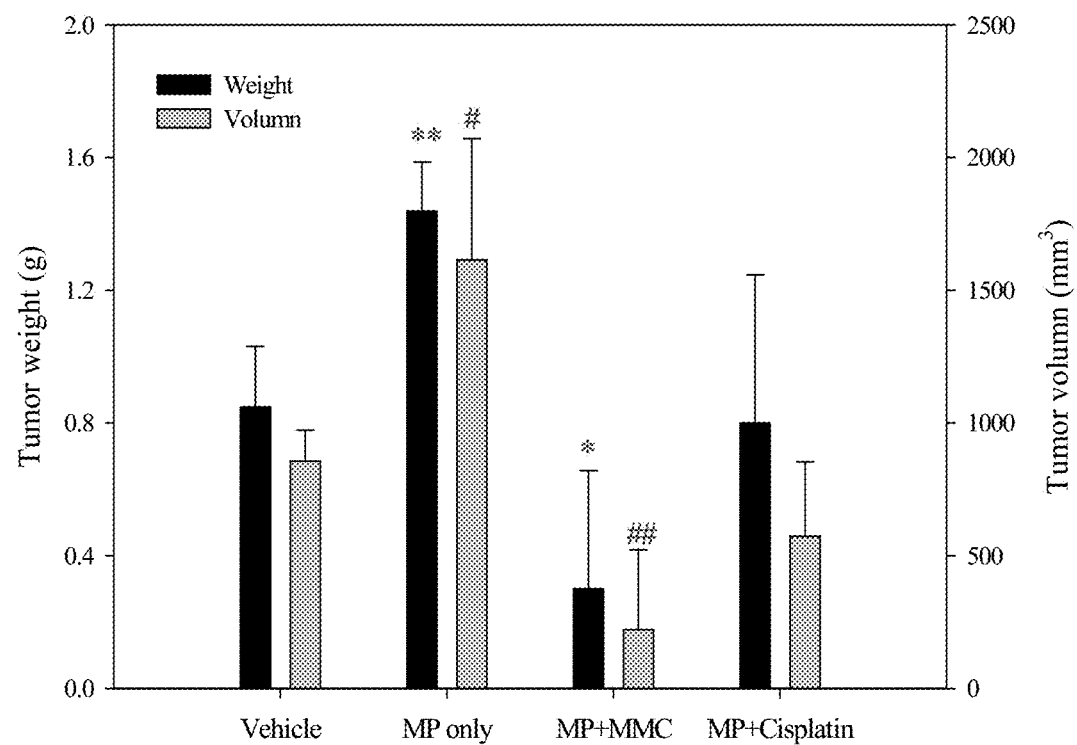

FIG. 26 shows the effect of MP load anti-cancer drug on growth rate of a tumor. (a) Tumor plot of each group. (b) Weight and volume of tumor of each group. Vehicle: normal saline (control), MMC: Mitomycin C (an anticancer drug).

Figure 27A:
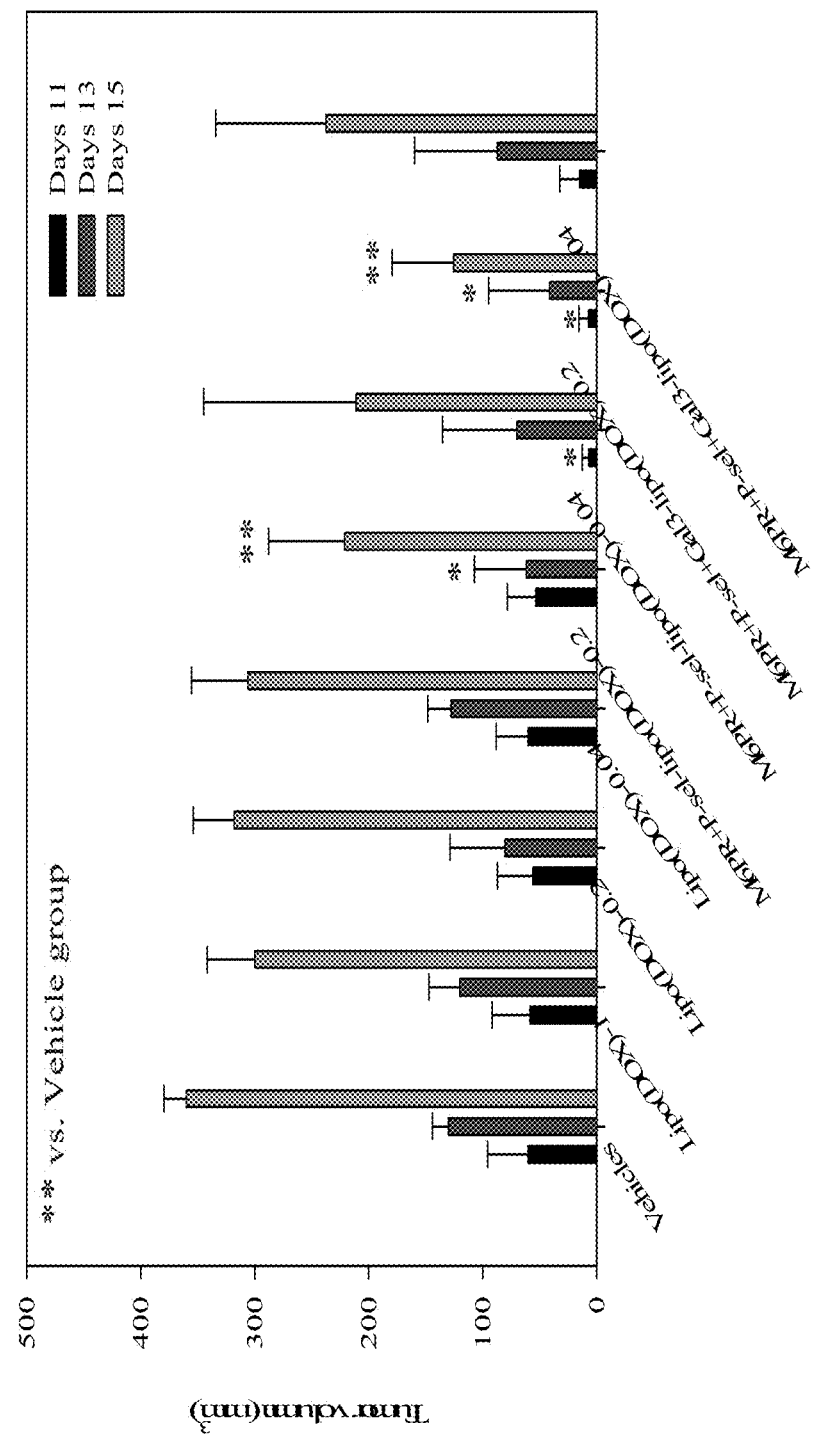

FIGS. 27(a) and (b) show that protein-conjugated engineered liposomes (containing doxorubicin) can inhibit tmopr growth rate (see FIG. 27(a)) and that also can reduce the mortality rate of the mice (FIG. 27(b)).

Figure 28:
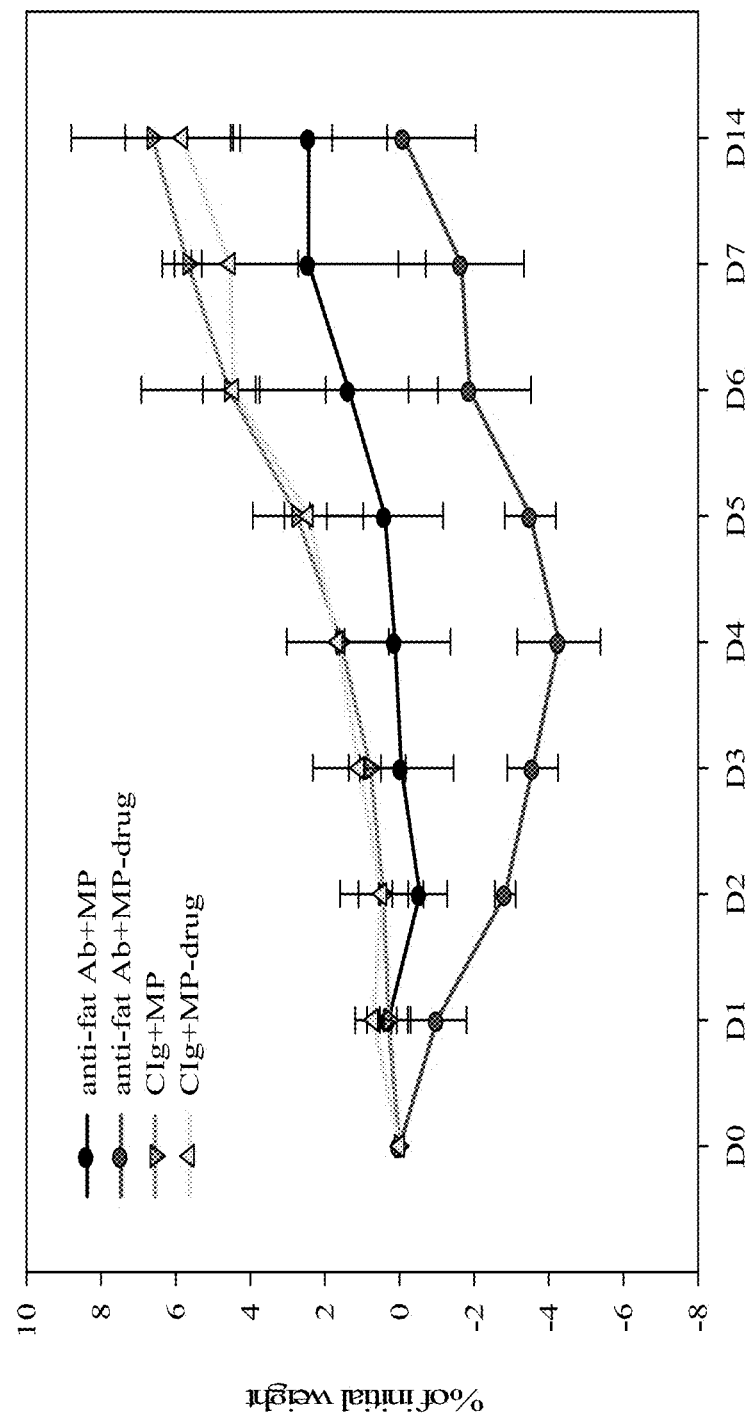

FIG. 28 shows the effect of liposomes load mitomycin C on fatty mice. Liposomes-drug: Liposomes loaded mitomycin C, CIg: Control Ig.

Figure 29A:
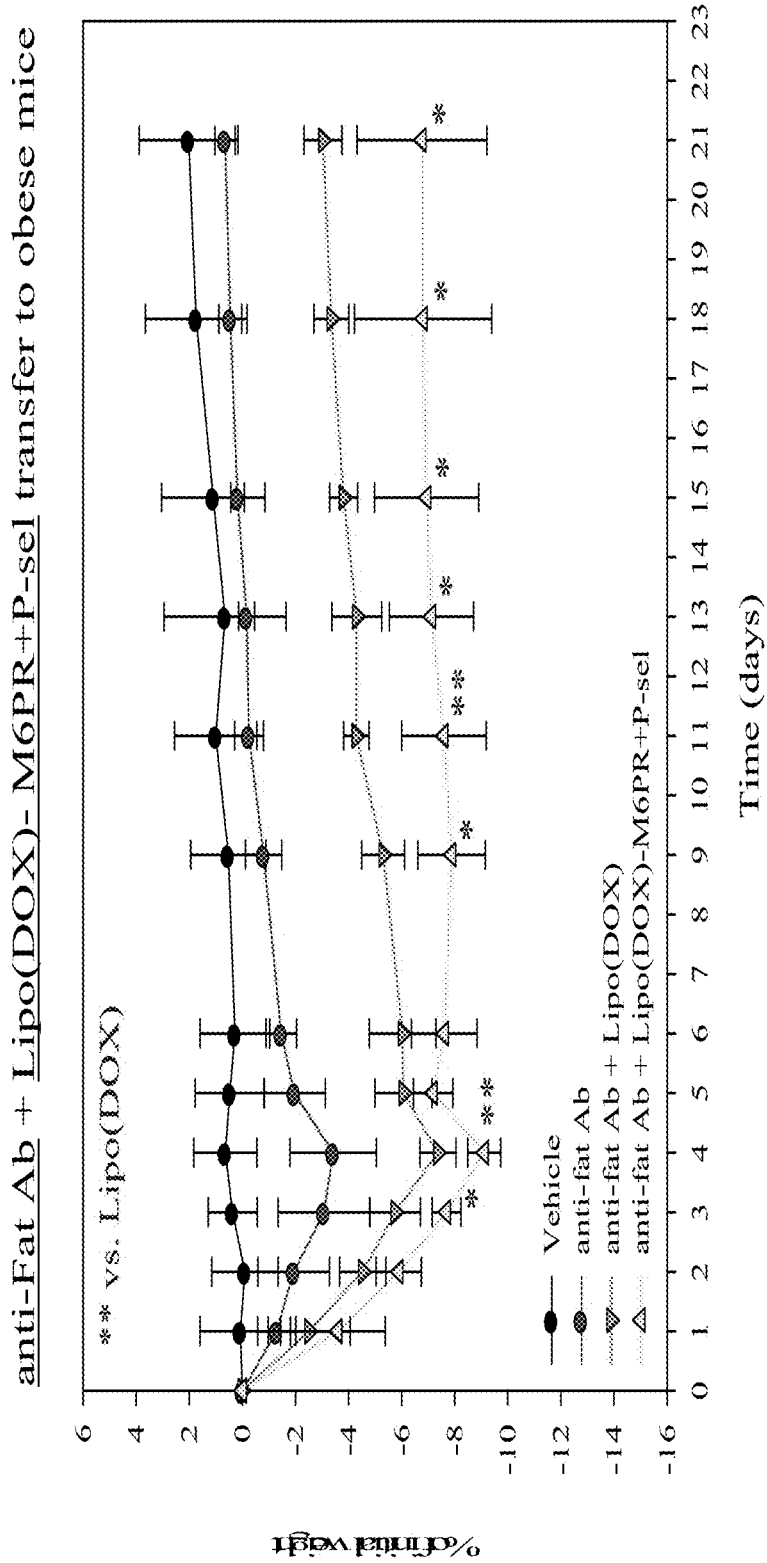

FIGS. 29(a) and (b) show that the protein-conjugated engineered liposomes (containing doxorubicin) can reduce the weight increasing rate of the mice (a). In addition, the anti-fat antibody or liposomes (containing doxorubicin) will not cause an increase in liver function index (b).

Figure 30:
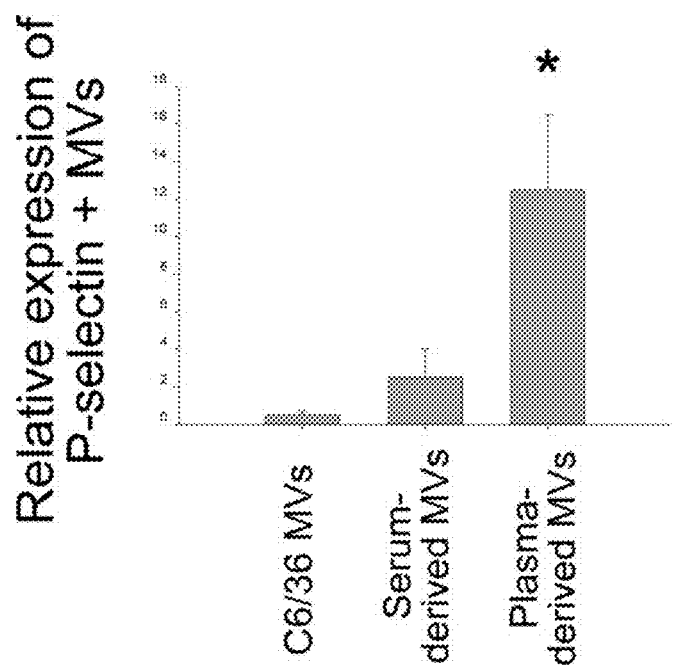

FIG. 30 shows that plasma MVs express P-selectin relative higher levels of surface P-selectin as compared to the serum and cell (C6/36)-derived MVs. Analyzed by flow cytometry. *$P<0.05$, compared to the serum-derived MV groups. (n=4).

Figure 31:
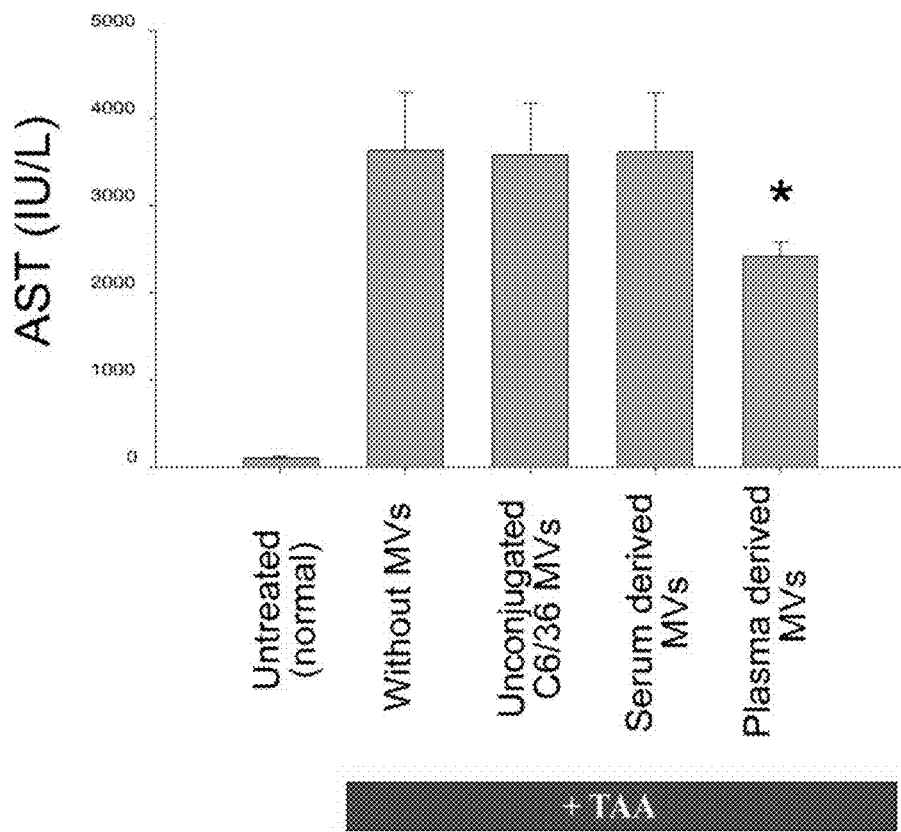

FIG. 31 shows plasma-derived MPs on the rescue of liver damage in TAA mouse model. (n=4).

Figure 32:
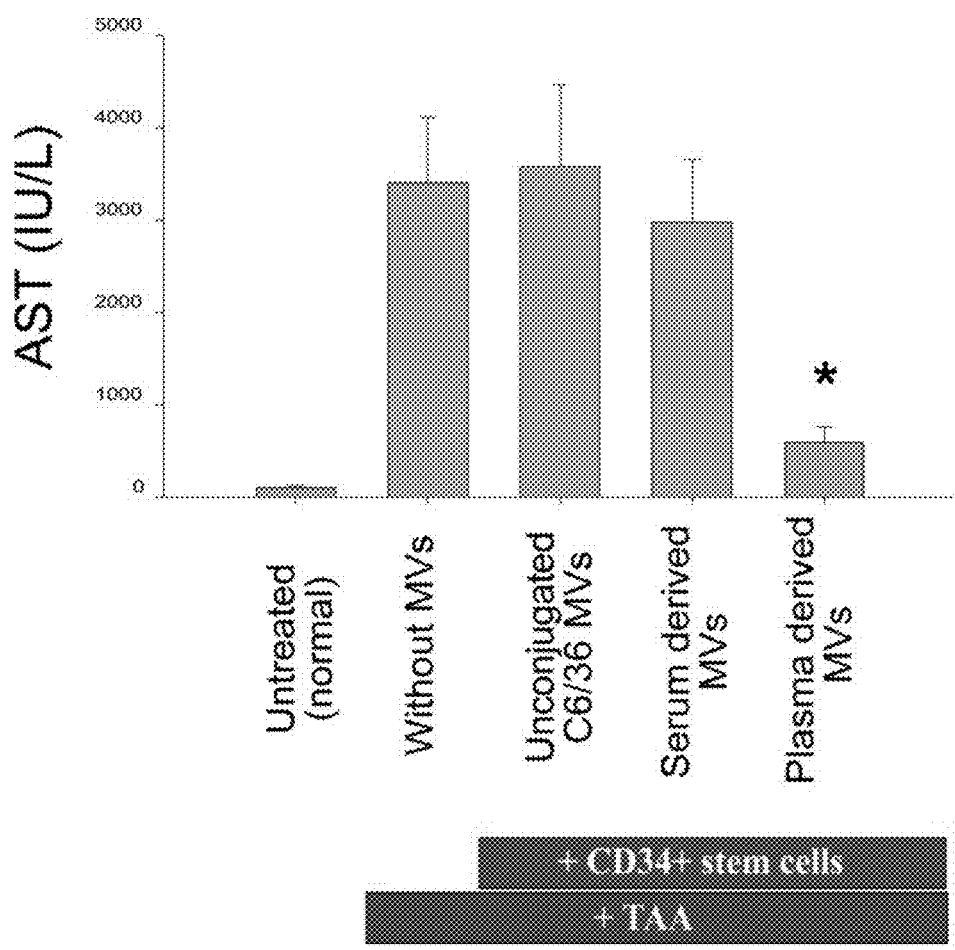

FIG. 32 shows the plasma hepatic enzyme AST levels, which indicated the liver function of the experimental mice, were indicated (the higher the AST levels indicate lower liver function). *$P<0.05$, compared to the serum-derived MV groups. (n=4). These results suggested that the plasma MVs are able to rescue the injury in the targeting tissues.

DETAILED DESCRIPTION OF THE INVENTION

The invention creates engineered surface protein expressed on or conjugated to vesicles for specific targeting and delivery of agents to autophagic and/or apoptotic cells. Particularly, the vesicles of the invention can achieve a synergistic effect on the targeting and drug delivery to autophagic and/or apoptotic cells and tissues containing the autophagic and/or apoptotic cells.

Where the definition of terms departs from the commonly used meaning of the term, applicant intends to utilize the definitions provided below, unless specifically indicated As used in this specification and the appended claims, the singular forms "a," "an" and "the" include plural referents unless the content clearly dictates otherwise.

As used herein, the use of "or" means "and/or" unless stated otherwise. In the context of a multiple dependent claim, the use of "or" refers back to more than one preceding independent or dependent claim in the alternative only.

As used herein, the term "one or more" is readily understood by one of skill in the art, particularly when read in context of its usage.

As used herein, the term "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

As used herein the term "micelle" refers to an aggregate (or supramolecular assembly) of surfactant molecules dispersed in a liquid colloid. A typical micelle in aqueous solution forms an aggregate with the hydrophilic "head" regions in contact with surrounding solvent, sequestering the hydrophobic single-tail regions in the micelle centre.

As used herein, the terms "agent" or "therapeutic agent" refers to an agent capable of treating and/or ameliorating a condition or disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "therapeutically effective amount" or "efficacious amount" refers to the amount of the vesicle that, when administered to a mammal or other subject for treating a disease, is sufficient to effect such treatment for the disease.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein, the term "conjugation site" refers to the site where a covalent linkage is formed between two macromolecules, mostly terminal-to-sidechain branched conjugations, and occasionally molecular head-to-tail linear conjugations.

In one aspect, the present invention provides a protein-conjugated vesicle, comprising one or more lectins or a fragment thereof expressed on or conjugated to the surface of the vesicle and optionally an agent.

In one embodiment, the agent is encapsulated within the vesicle or attach to outer surface of the vesicle.

In some embodiments, the vesicle is a liposome or a micelle. The vesicle can be artificially engineered or cell-derived.

In some embodiment, the lectin or a fragment thereof is selected from the group consisting of cation-dependent mannose-6-phosphate receptor (M6PR), P-selectin, E-selectin, L-selectin, P-selectin-ligand-1 (PSGL-1), CD22, CD206, galectin 3, annexin V, CD31, integrin αLβ2, VE-cadherin, CD300a, CD47, thrombospondin 1 (TSP1) and CD36, or a fragment thereof. In some embodiments, M6PR, P-selectin, E-selectin, P-selectin-ligand-1 (PSGL-1), CD22, CD206, galectin 3, annexin V, integrin αLβ2, VE-cadherin alone are sufficient to conduct the vesicle targeting to autophagic and/or apoptotic cells and autophagic and/or apoptotic cells-containing tissues and serve as the first proteins (EPs). In further some embodiments, the vesicle comprises M6PR in combination with P-selectin, E-selectin, PSGL-1 or galectin 3; or Siglec 2 in combination with P-selectin or galectin 3.

In some embodiments, CD300a, CD47, thrombospondin 1 (TSP1) and CD36 can be further serve as the second proteins. Accordingly, the invention further provides a vesicle comprising one or more the first proteins selected from the group consisting of M6PR, P-selectin, E-selectin, L-selectin, P-selectin-ligand-1 (PSGL-1), CD22, CD206, galectin 3, annexin V, CD31, integrin αLβ2 and VE-cadherin and one or more the second proteins selected from the group consisting of CD300a, CD47, thrombospondin 1 (TSP1), Toll like receptor 4 (TLR4) and CD36 and a fragment thereof. In some embodiments, the vesicle comprises M6PR or P-selectin in combination with TLR4, galectin 3, CLEC2, Integrin αLβ2 or CD31. The vesicle with the combination of protein labeling can achieve a synergistic effect on the targeting and drug delivery to autophagic and/or apoptotic cells and autophagic and/or apoptotic cells-containing tissues. The synergistic effect on the targeting effect reduces the effective dosage of the agent to be delivered and thus the side effect of the drug can be reduced.

In one embodiment, the agent is a diagnostic agent or a therapeutic agent. In one embodiment, the agent is an autophagic or apoptotic drug. In some embodiments, examples of the agent include, but are not limited to, an antimalarial drug, an autophagy inhibitor, a histone deacetylase (HDAC) inhibitor, an antagonist of the EP or AP described herein, a diagnostic contrast agent, a cell survival enhancing agent (or a cell death suppressing agent), a cell survival suppressing agent (or a cell death enhancing agent), a cell (such as stem cell and progenitor cell), a cell component, an organelle, a cytotoxic agent, an antitumor drug, a toxin or an antibody a lipid, a protein, DNA, RNA, a therapeutic agent and a nanomaterial. In one embodiment, the antagonist of the aforementioned first protein or second protein (such as the soluble form, corresponding ligand and the neutralizing and blocking antibody) is able to serve as antidotes to reduce the vesicle-targeting to autophagic and apoptotic cells and autophagic and apoptotic cells-containing tissues. In some embodiment, the agent is bardoxolone methyl, chloroquine, quinine, hydrochloroquine, sorafenib, sunitinib, Hsp90 inhibitor, metformin or crizotinib.

Liposomes provided herein include unilamellar liposomes, multilamellar liposomes and multivesicular liposomes. Liposomes provided herein may be composed of positively charged, negatively charged or neutral phospholipids.

A liposome used in the invention can be made by different methods known in the art. For example, a phospholipid such as the neutral phospholipid dioleoylphosphatidylcholine (DOPC), Dipalmitoyl Phosphatidylcholine (DPPC) and/or EPC, can be dissolved in an alcohol or other organic solvent and then mixed with a component for inclusion in the lipid bilayer. The mixture may further include various detergents. Typically, a lipid mixture is vortexed, frozen in a dry ice/acetone bath and lyophilized overnight. The lyophilized preparation is stored at −20° C. or less for extended periods of time. When required the lyophilized liposomes are reconstituted.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 minutes to 2 hours, depending on the desired volume of the liposomes. The composition can be dried further in a desiccator under vacuum. The dried lipids generally are discarded after about 1 week because of a tendency to deteriorate with time.

Micelle structure will itself be determined, in large part, by the types and compositions of polymer molecules used to form the micelle and the solvent environment of the micelle. In some embodiments, micelles are fabricated using non-ionic triblock co-polymers consisting of both hydrophilic and hydrophobic monomer units. In embodiments of the present disclosure, a poloxamer, a triblock copolymer of poly (ethylene oxide)-poly(propylene oxide)-poly(ethylene oxide) (PEO-PPO-PEO) is used. In some embodiments, the micelles of this disclosure can be prepared using PEG-PLA polymers of a variety of block sizes (e.g., a block size within a range described above) and in a variety of ratios (e.g., PEG:PLA of about 1:10 to about 10:1, or any integer ratio within said range).

The conjugation of the protein described herein into the vesicle is through a supplement of functional-group labeled lipid into the vesicle using the shear force-based methods (Yu B, Lee R J, Lee L J *Microfluidic methods for production of liposomes. Methods Enzymol.* 2009; 465:129-141; and Jeong D, Jo W, Yoon J, et al. *Nanovesicles engineered from ES cells for enhanced cell proliferation. Biomaterials.* 2014; 35(34):9302-9310).

In another aspect, the invention provides a pharmaceutical composition comprising a vesicle of the invention and a pharmaceutically acceptable carrier. The vesicles of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 20.sup.th ed., 2003, supra). Effective formulations include oral and nasal formulations, formulations for parenteral administration, and compositions formulated for with extended release.

For purposes of administration, for example, parenteral administration, sterile aqueous solutions of water-soluble salts (e.g., NaCl) can be employed. Additional or alternative carriers may include sesame or peanut oil, as well as aqueous propylene glycol. Aqueous solutions may be suitably buffered, if necessary, and the liquid diluent can first be rendered isotonic with sufficient saline or glucose. These aqueous solutions are especially suitable for intravenous, intramuscular, subcutaneous, intraperitoneal, and intratumoral (IT) injection.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

In another aspect, the present invention provides a method for targeting delivery of an interested agent to an autophagic and/or apoptotic cell or a tissue containing the cell, comprising administering a protein-conjugated vesicle of the invention to a subject. In one embodiment, before administration of the vesicle, the method additionally comprises a step of administering an autophagic and/or apoptotic inducing agent to a target cell or a target tissue. By using the step, the target cell or tissue would occur autophagic or apoptosis so that the vesicle of the invention can target to the autophagic and/or apoptotic cell or tissue and then deliver the interested agent to the cell or tissue. For example, an anti-obesity antibody is administered to a subject first so that the adipose cells or tissues are autophagic and/or apoptotic; then the vesicle with an anti-obesity drug is administered to target the autophagic and/or apoptotic adipose cells or tissues so that the adipose cells or tissues can be further damaged by the anti-obesity drug.

Autophagy is a lysosomal degradation pathway that is essential for survival, differentiation, development, and homeostasis. The delivery of an agent or a therapeutic agent with the vesicle of the invention to autophagic cells is directed to a disease associated with autophagy deregulation. The disease associated with autophagy deregulation includes but is not limited to, trauma, exposure to chemical and physical toxic factors, genetic disease, age-related disease, cardiovascular disease, infectious disease, neoplastic disease, neurodegenerative disease, metabolic disease, aging (when ATG5 is overexpressed in the entire organism), obesity (when ATG7 or the pro-autophagic transcription factor EB [TFEB] are overexpressed in hepatocytes), cancer (when beclin 1 is expressed in KRAS-induced lung adenomas), neurodegeneration induced by β-amyloid or α-synuclein or toxicity (when TFEB or beclin 1 are overexpressed in the brain or when cystatin B, an inhibitor of lysosomal cysteine proteases, is knocked out), myodegenerative conditions (when TFEB or beclin 1 are targeted to the skeletal muscle), and chronic lung inflammation caused by cystic fibrosis (when beclin 1 is expressed in the lung).

Apoptosis is controlled by the integration of multiple pro- and anti-apoptotic signals. The delivery of an agent or a therapeutic agent with the vesicle of the invention to apoptotic cells is directed to a disease associated with apoptosis alteration. The disease associated with apoptosis alteration includes but is not limited to, trauma, exposure to chemical and physical toxic factors, genetic disease, age-related disease, age-related disease, cardiovascular disease, infectious disease, neoplastic disease, neurodegenerative disease, metabolic disease, aging, obesity, cancer, neurodegeneration induced by β-amyloid or α-synuclein (alzheimer, parkinson, huntington, amyotrophic lateral sclerosis) or toxicity, myodegenerative conditions, or chronic lung inflammation caused by cystic fibrosis, cardiovascular disorder (such as ischemia, heart failure and infectious disease) and autoimmune disease (systemic lupus erythematosus, autoimmune lymphoproliferative syndrome, rheumatoid arthritis and thyroiditis).

The vesicles of the present invention can be used to treat or diagnose any disease requiring the administration of a diagnostic agent or a therapeutic agent. Any suitable agent or therapeutic agent can be used with the vesicles of the present invention. In addition, the vesicles of the present invention are useful for the treatment of infection by pathogens such as viruses, bacteria, fungi, and parasites. Other diseases can be treated using the vesicles of the present invention.

In some embodiments, the vesicle or pharmaceutical composition of the invention can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In some embodiment, the protein-conjugated vesicle can deliver a lipid, a protein, DNA, RNA, a therapeutic agent or a nanomaterial. In some embodiments, the therapeutic agent is a cell survival enhancing agent (or a cell death suppressing agent). The delivery of a cell survival enhancing agent (or a cell death suppressing agent to a subject is able to conduct a drug-mediated rescue of tissue injury.

In some embodiments, the agent is a cell survival suppressing agent, cell death enhancing agent or antitumor agent. The delivery of a cell survival suppressing agent (cell death enhancing agent) or antitumor agent is able to reduce target cell survival of those tissues containing naturally occurred autophagy and apoptotic cells such as tumors or reduce the selected specific tissue wherein the autophagy and apoptotic cells are artificially induced in the specific tissues using cytotoxic agents such as a drug, a toxin or an antibody against tissue-specific proteins.

In some embodiments, the therapeutic agent is a stem cell or a progenitor cell. The delivery of stem cells and progenitor cells are able to exert protective physiological functions and rescue autophagic and apoptotic cell-containing tissues.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. The following examples are provided for the intent of illustrating embodiments and advantages of the invention and are not intended to limit its scope.

EXAMPLE

Example 1

Liposome Targeting to Aautopahgic Cells In Vitro

Liposomes Preparation

The liposomes were prepared by liposome kits (Sigma-Aldrich Co.) and respective lipids. The conjugation of surface proteins is through supplements of functional-group labeled lipids into the liposomes using the shear force-based methods (Yu B, Lee R J, Lee L J *Microfluidic methods for production of liposomes. Methods Enzymol.* 2009; 465:129-141; and Jeong D, Jo W, Yoon J, et al. *Nanovesicles engineered from ES cells for enhanced cell proliferation. Biomaterials.* 2014; 35(34):9302-9310). The protein conjugation of proteins (M6PR, P-selectin, E-selectin, PSGL-1, CD22, CD206, galectin 3, annexin V, integrin αLβ(32, VE-cadherin, CD300a, CD47, TSP1 and CD36) to the liposomes is 45 based to the methods provided by the manufacture.

Determination of the Relative Engagement Levels Toward the Autophagy and Apoptotic Cells The mouse B16-F10 cells were suspended for 4 hours to induce autophagy and apoptosis. The autophagy and apoptosis cell were labeled with green fluorescent dyes (GFDs), using Cyto-ID autophagy detection kit (Enzo Life Sciences)

Figure 1:
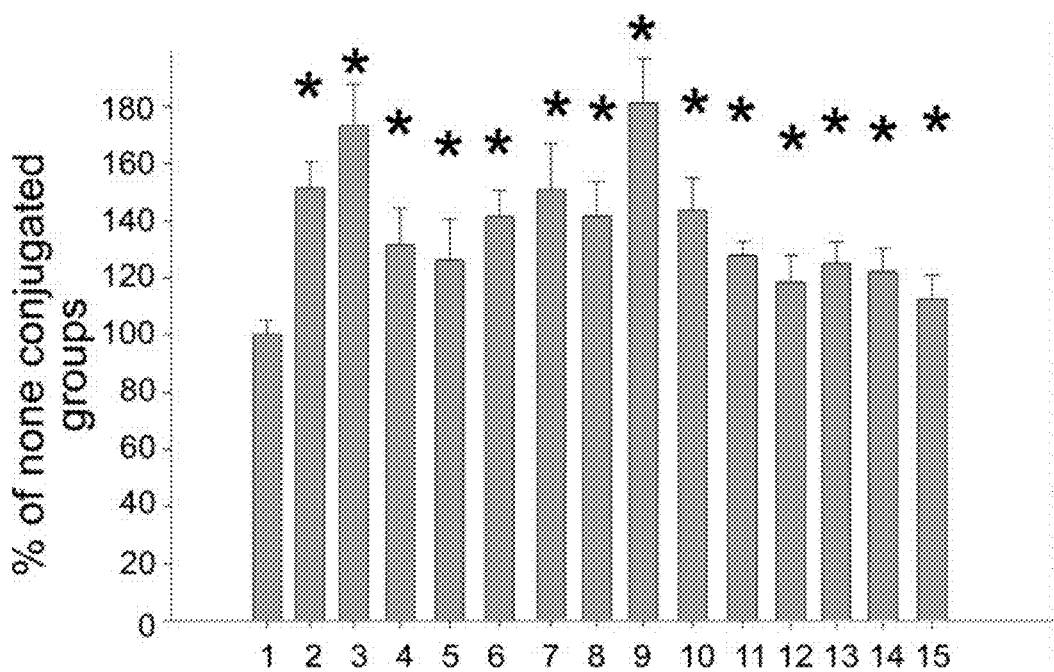
FIG. 1 shows liposome targeting to autopahgic cells in vitro. *P<0.05 vs. none groups (n=3). Groups 1-15 displayed cell-bound levels of various liposomes with or without protein conjugations. Groups: 1, unconjugated; 2, M6PR; 3, P-selectin; 4. E-selectin; 5, PSGL-1; 6, CD22; 7, CD206; 8, galectin 3; 9, annexin V; 10, integrin αLβ2; 11, VE-cadherin; 12, CD300a; 13, CD47; 14, TSP1 and CD36, conjugated liposomes. Unconjugated groups were normalized to 100%.
Figure 2:
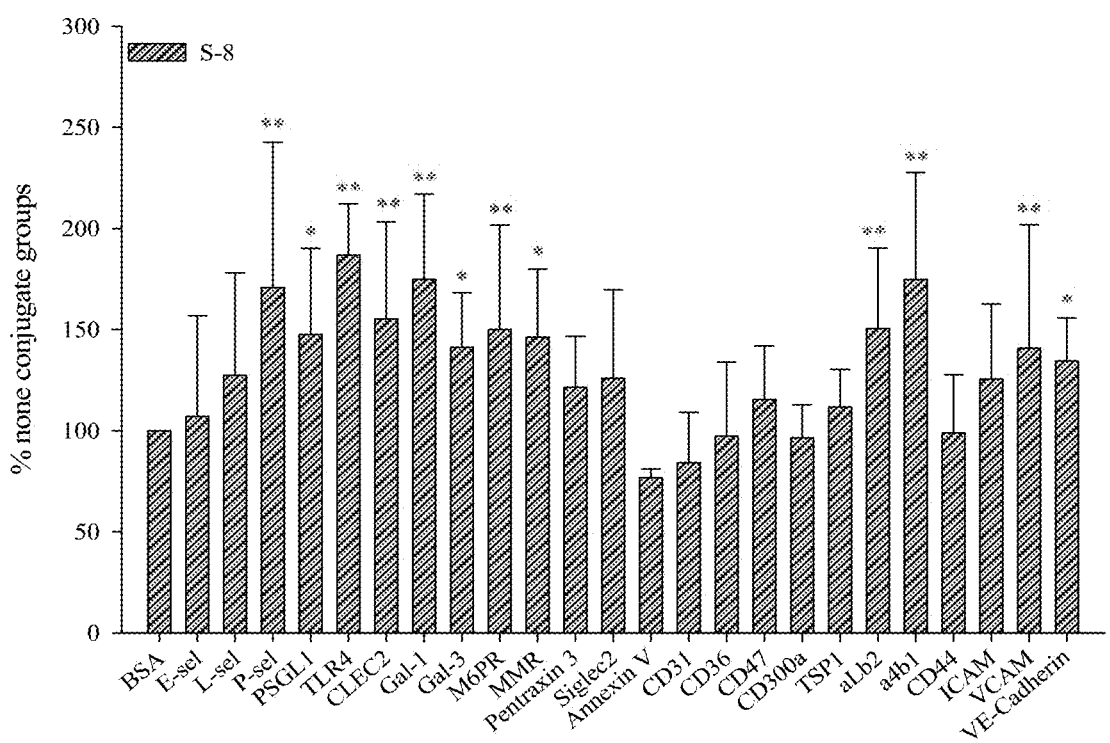
FIG. 2 shows liposome targeting to apoptotic cells in vitro. *P<0.05 vs. none groups (n=3). Groups 1-15 displayed cell-bound levels of various liposomes with or without protein conjugations. Groups: 1, unconjugated; 2, M6PR; 3, P-selectin; 4. E-selectin; 5, PSGL-1; 6, CD22; 7, CD206; 8, galectin 3; 9, annexin V; 10, integrin αLβ2; 11, VE-cadherin; 12, CD300a; 13, CD47; 14, TSP1 and CD36, conjugated liposomes. Unconjugated groups were normalized to 100%.
Figure 3:
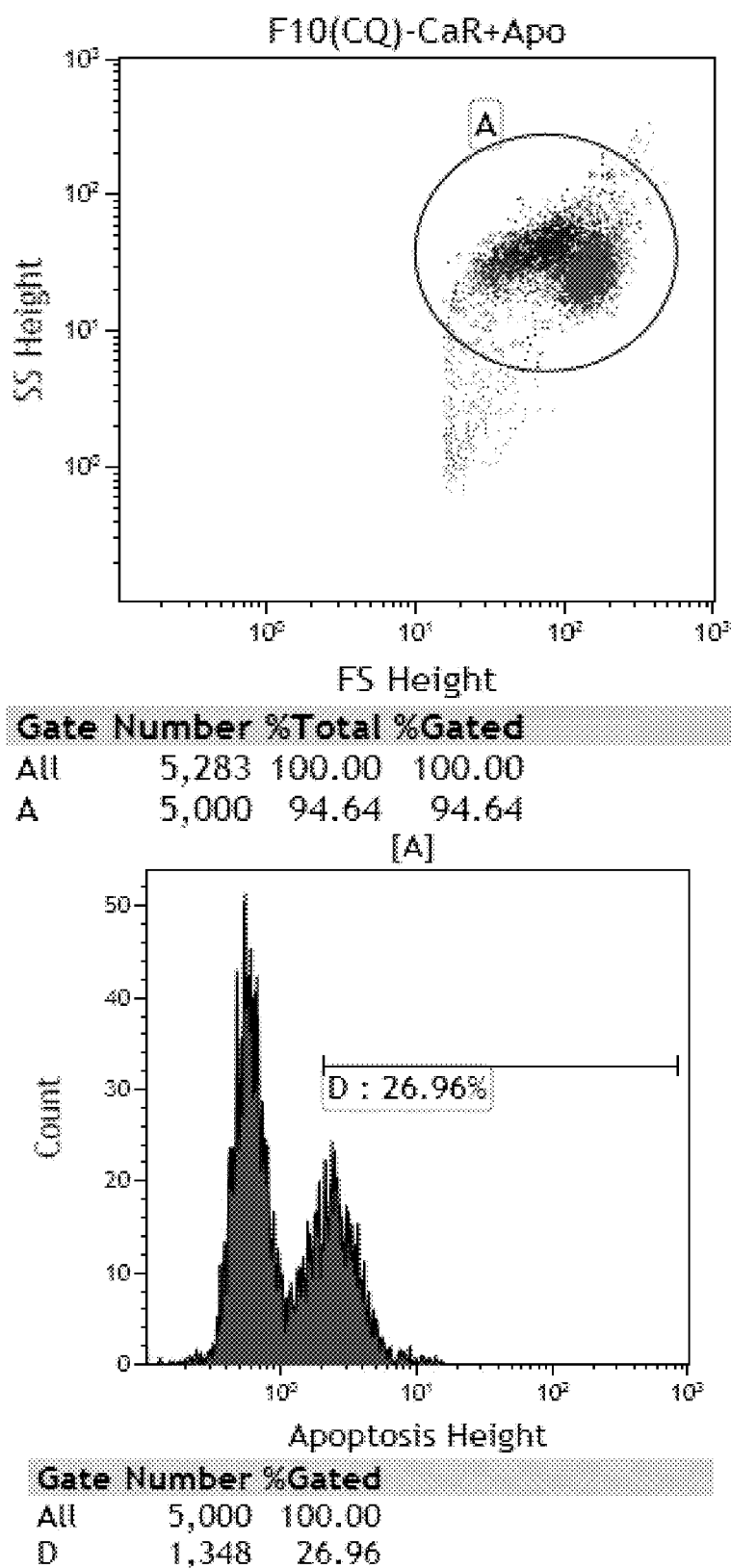
FIG. 3 shows an example of flow cytometry analysis and detection of autophagy cells (the blue population).
Figure 4:
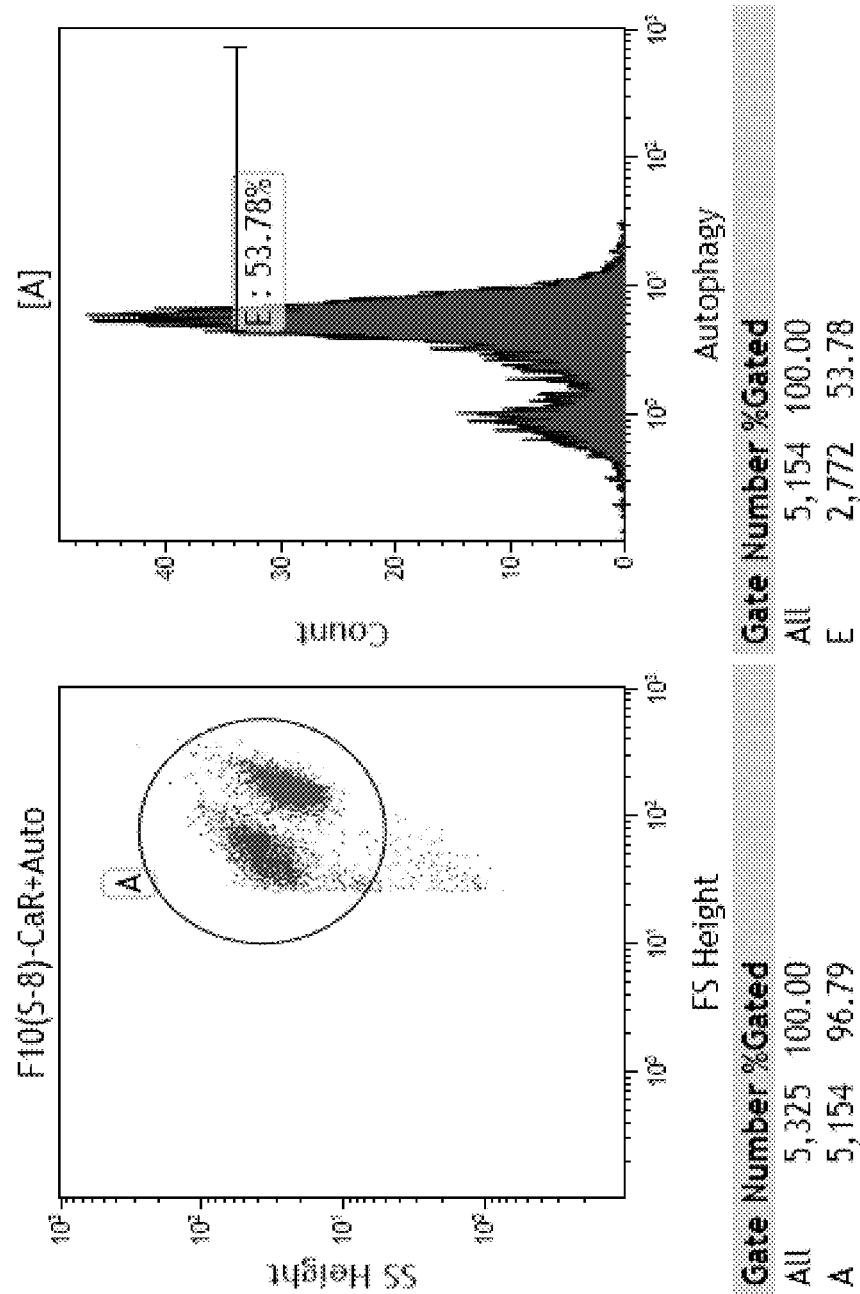
FIG. 4 shows an example of flow cytometry analysis and detection of apoptotic cells (the purple population).

(see FIG. 1 and FIG. 3) and CaspGLOW™ Red Active Caspase-3 Staining Kit (BioVision) (see FIG. 2 and FIG. 4) kits, respectively. The autophagy and apoptosis cell containing populations were engaged with various protein conjugated liposomes, which were labeled with fluorescent dye calcein-red (CR). The percentage of B16-F10-liposome engaged populations (GFD and CR double positive populations) were determined using flow cytometry. The levels of liposomes and fluorescent beads engaged with none conjugated cells (the "unconjugated" groups) were normalized to 100% (see FIG. 1 and FIG. 2).

Example 2

Figure 5:
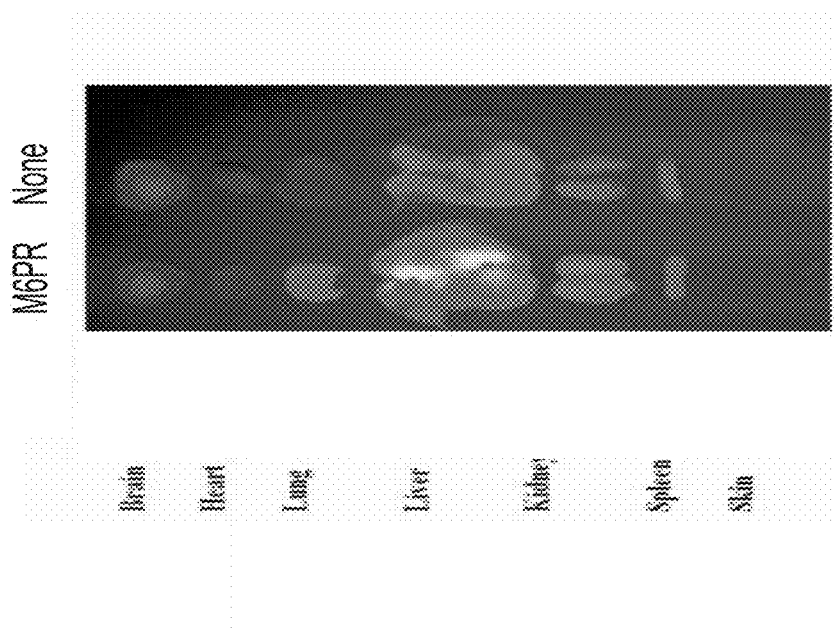
FIG. 5 shows the targeting effect of recombinant protein conjugated liposomes by in vivo image system (IVIS). The fluorescent intensity of recombinant M6PR conjugated liposome (label fluorescent dye calcein Red).

Liposomes Specifically Targeted to the Injury Tissues Through Various Protein Conjugates Targeting of Engineered Liposomes to Injured Liver in Thioacetamide (TAA) Hepatitis Mouse Model In thioacetamide (TAA) hepatitis mouse model, the non-conjugated liposomes (contain fluorescein) and M6PR-conjugated engineered liposomes (contain fluorescein) were intravenously injected into the experimental mice, respectively. At 24 h after the fluorescence levels were determined using an IVIS system (see FIG. 5). These results suggested that the M6PR-conjugated engineered liposomes (contain fluorescein) can specific deliver liposome-loaded fluorescein into liver.

Figure 6:
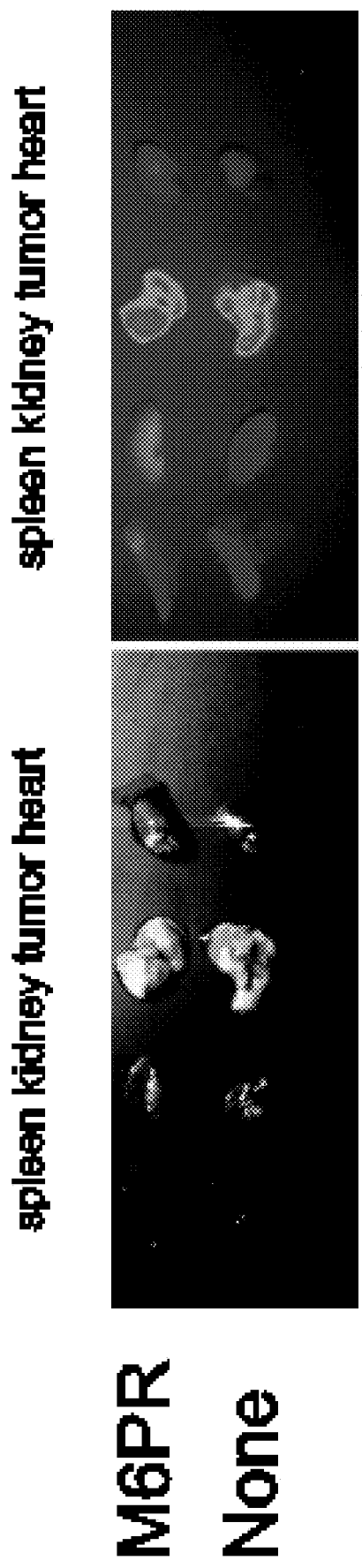
FIG. 6 shows the targeting effect of recombinant protein conjugated liposomes on B16-F10 tumor cell by in vivo image system (IVIS). Fluorescence-labeled liposomes were used. The fluorescent intensity of recombinant M6PR protein conjugated liposomes (label fluorescent dye calcein Red). None: treated with unconjugated liposomes.

A synergistic assay was performed according to the above-mentioned method. The results are shown in FIG. 6. As shown in the figure, the fluorescence intensity of M6PR in combination with P-sel, gal-3, siglec2, MMR, αLβ2, CD31, annexin V, CD44 or VE-Cadherin in liver is significantly higher than M6PR only. The above combinations exhibit a synergistic effect.

The Solid Tumor Derived from Mouse B16-F10 Cell Line

Figure 7:
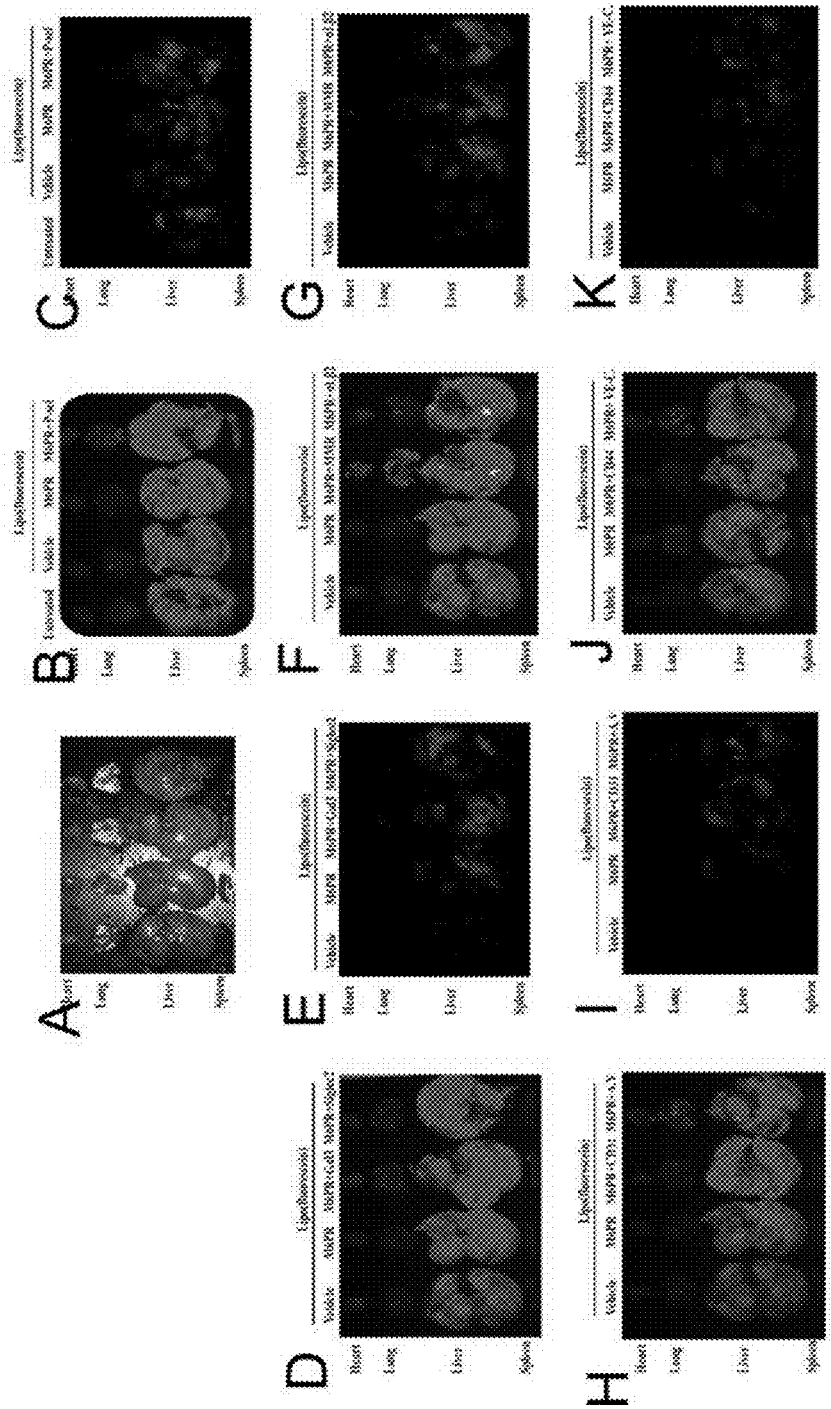
FIG. 7 shows that an in vivo image system (IVIS) was used to identify whether recombinant protein-conjugated fluorescent liposome has targeting effect on injured liver.

The mice were subcutaneously injected with B16-F10 melanoma cell ($1*10^6$ cell/mice) to groin site. At the third day and eighth day, the control liposomes and M6PR-conjugated engineered liposomes (containing fluorescein) were injected to the orbital sinus of the mice, respectively. The mice were sacrificed at the twelfth day. The fluorescence intensities of the tumors were observed using the IVIS® Spectrum and the results are shown in FIG. 7. As shown in the figure, the fluorescence intensity of M6PR-conjugated engineered liposomes in tumors is significantly higher than that in other organs, which shows that M6PR conjugated engineered liposomes can identify tumor site.

A synergistic assay was performed according to the above-mentioned method. The control liposomes, M6PR, M6PR-P-sel-conjugated liposomes and M6PR-Gal3-conjugated engineered liposomes (containing fluorescein) were injected to the orbital sinus of the mice, respectively. The mice were sacrificed at the twelfth day. The fluorescence intensities of the tumors were observed using the IVIS® Spectrum and the results are shown in FIG. 8. As shown in the figure, the fluorescence intensities of M6PR, M6PR-P-sel-conjugated liposomes and M6PR-Gal3-conjugated engineered liposomes in tumors are significantly higher than that in other organs. Moreover, M6PR-P-sel liposomes and M6PR-Gal3-conjugated engineered liposomes exhibit better synergistic efficacy than M6PR-conjugated engineered liposomes.

The Adipose Tissue after Anti-Fat Antibody Injections

The mice with high fat diet were injected with the control Igs or anti-fat antibody (75 µg/mice) to orbital sinus at 0 and 48 hours, respectively. The control liposomes, M6PR, M6PR-P-sel-conjugated liposomes and M6PR-Gal3-conjugated engineered liposomes (containing fluorescein) were injected to the orbital sinus of the mice at 6, 24, 54 and 72 hours, respectively. The mice were sacrificed after 96 hours to take out the white adipose tissue. The fluorescence intensities of the tumors were observed using the IVIS® Spectrum and the results are shown in FIG. 9. As shown in the figure, the fluorescence intensities of M6PR, M6PR-P-sel-conjugated liposomes and M6PR-Gal3-conjugated engineered liposomes in the fat tissues are significantly higher than the control. Moreover, M6PR-P-sel liposomes and M6PR-Gal3-conjugated engineered liposomes exhibit better synergistic efficacy than M6PR-conjugated engineered liposomes.

The Injury Tissues Contain Autophagic and Apoptotic Cells. Thioacetamide (TAA) Treated Mouse Liver In thioacetamide (TAA) hepatitis mouse model, the non-conjugated liposomes (contain fluorescein) and M6PR-conjugated engineered liposomes (contain fluorescein) were intravenously injected into the orbital sinus of the experimental mice, respectively. At 24 hours after the autophagy and apoptosis liver cell were labeled with green fluorescent dyes (GFDs), using Cyto-ID autophagy detection kit (Enzo Life Sciences) and CaspGLOW™ Red Active Caspase-3 Staining Kit (BioVision) kits, respectively. The autophagy and apoptosis liver cell containing populations were engaged with M6PR-conjugated engineered liposomes, which were labeled with fluorescent dye calcein-red (CR). The percentage of liver cell-liposome engaged populations (GFD and CR double positive populations) were determined using flow cytometry. The levels of liposomes and fluorescent beads engaged with none conjugated cells (the "unconjugated" groups) were normalized to 100% (see FIG. 10).

Solid Tumor Formed by B16-F10 Cells

The mice were subcutaneously injected with B16-F10 melanoma cell ($1*10^6$ cell/mice) to groin site. At the third day and eighth day, the control liposomes and M6PR-conjugated engineered liposomes (containing fluorescein) were injected to the orbital sinus of the mice. The mice were sacrificed at the twelfth day. The autophagy and apoptosis tumor cell were labeled with green fluorescent dyes (GFDs), using Cyto-ID autophagy detection kit (Enzo Life Sciences) and CaspGLOW™ Red Active Caspase-3 Staining Kit (BioVision) kits, respectively. The autophagy and apoptosis tumor cell containing populations were engaged with M6PR-conjugated engineered liposomes, which were labeled with fluorescent dye calcein-red (CR). The percentage of liver cell-liposome engaged populations (GFD and CR double positive populations) were determined using flow cytometry. The levels of liposomes and fluorescent beads engaged with none conjugated cells (the "unconjugated" groups) were normalized to 100% (see FIG. 11).

Anti-Fat Antibody Treated Adipose Tissue

The mice with high fat diet were injected with the control Igs or anti-fat antibody (75 µg/mice) to orbital sinus at 0 and 48 hours, respectively. The control liposomes, M6PR, M6PR-P-sel-conjugated liposomes and M6PR-Gal3-conjugated engineered liposomes (containing fluorescein) were injected to the orbital sinus of the mice at 6, 24, 54 and 72 hours, respectively. The mice were sacrificed after 96 hours to take out the white adipose tissue. The autophagy and apoptosis adipocyte were labeled with green fluorescent dyes (GFDs), using Cyto-ID autophagy detection kit (Enzo Life Sciences) and CaspGLOW™ Red Active Caspase-3 Staining Kit (BioVision) kits, respectively. The autophagy and apoptosis adipocyte containing populations were engaged with M6PR-conjugated engineered liposomes, which were labeled with fluorescent dye calcein-red (CR). The percentage of liver cell-liposome engaged populations (GFD and CR double positive populations) were determined using flow cytometry. The levels of liposomes and fluorescent beads engaged with none conjugated cells (the "unconjugated" groups) were normalized to 100% (see FIG. 12).

Example 3

Treatments of Blocking Antibodies, Soluble Recombinant Proteins and Soluble M6P are Able to Block the Targeting of M6PR-Conjugated Engineered Liposomes/Microvesicles Targeting to the Autophagy and Apoptotic Cells and May Serve as the Antidotes The mouse B16-F10 cells were suspended for 4 hours and then treated with blocking antibody or soluble M6PR recombinant protein plus additional M6PR+P-selectin-conjugated liposomes. The autophagy and apoptosis cell were labeled with green fluorescent dyes (GFDs), using Cyto-ID autophagy detection kit (Enzo Life Sciences) and Casp-GLOW™ Red Active Caspase-3 Staining Kit (BioVision) kits, respectively. The autophagy and apoptosis cell containing populations were engaged with M6PR+P-selectin-conjugated liposomes, which were labeled with fluorescent dye calcein-red (CR). The percentage of B16-F10-liposome engaged populations (GFD and CR double positive populations) were determined using flow cytometry. The levels of liposomes and fluorescent beads engaged with none conjugated cells (the "unconjugated" groups) were normalized to 100% (see FIG. 13 and FIG. 14).

Example 4

Liposome Loaded Materials (Lipid, DNA, RNA, Protein, Drug) Specifically Targeted to Autophagic and Apoptotic Cells In Vitro The mouse B16-F10 cells were suspended for 4 hours to induce apoptosis and then treated with Caspase-3 inhibitor-loaded M6PR-conjugated liposomes and were incubated with a serum free medium. At 24 h after the percentage of apoptotic cells were determined using flow cytometry (see FIG. 17).

Molecular Probes® labeling chemistries (DNA, RNA and Protein Labeling Kits; ThermoFisher Scientific Co.) were used to prepare fluorescence-labeled DNA, RNA and protein. Fluorescent DNA, RNA and protein (Bcl-xL BH4 motif) were delivered to liposomes/MVs through complex or conjugated (glutaraldehyde; Sigma-Aldrich Co.) with cell penetrating peptide R8 11. These results M6PR-conjugated liposomes are able to achieve targeting of DNA, RNA and protein loaded liposomes to the apoptotic cells (see FIG. 18).

TABLE 1

Using caspase-3 inhibitor loaded liposomes that conjugated with a single recombinant protein as examples to analyze the synergistic rescue of TAA treated mice through detecting by reduced ALT levels (+ $P < 0.05$, ++ $P < 0.01$).

| EP | EP | | | | | | | |
|---|---|---|---|---|---|---|---|---|
| | P-sel | E-sel | PSGL-1 | Gal 3 | CD22 | CD206 | Integrin αLβ2 | VE-cadherin |
| M6PR | ++ | ++ | + | ++ | ++ | + | + | + |

TABLE 2

Using caspase-3 inhibitor loaded liposomes that conjugated with M6PR plus a second protein as examples, to analyze the synergistic rescue of TAA treated mice through detecting by reduced ALT levels (+ $P < 0.05$, ++ $P < 0.01$).

| | AP | | | | |
|---|---|---|---|---|---|
| EP | annexin V | CD300a | CD36 | CD47 | TSP1 |
| M6PR | ++ | ++ | ++ | + | + |

Example 6

Demonstration of Engineered Liposomes Specifically Targeted to the Injury Tissues (IVIS) Through Various Protein Conjugates on Liposomes In Vivo In thioacetamide (TAA) hepatitis mouse model, theM6PR, M6PR+P-selectin-, M6PR+E-selectin- and M6PR+PSGL-1-conjugated, caspase-3 inhibitor-loaded liposomes were intravenously injected into the experimental mice. At 24 h after the plasma aspartate transaminase (AST) levels were analyzed (see FIG. 19). These results suggested that the selectin-conjugated liposomes are not only able to target to injured tissues, but also are able to carry drugs to cure target tissues (see FIG. 19).

In thioacetamide (TAA) hepatitis mouse model, the M6PR, M6PR+P-selectin-, M6PR+E-selectin- and M6PR+PSGL-1-conjugated, Bcl-2 expression plasmid-loaded liposomes were intravenously injected into the experimental mice. At 24 h after the plasma aspartate transaminase (AST) levels were analyzed (see FIG. 20). These results suggested that the selectin-conjugated liposomes are not only able to target to injured tissues, but also are able to carry plasmid DNA to cure target tissues.

In thioacetamide (TAA) hepatitis mouse model, the M6PR, M6PR+P-selectin-, M6PR+E-selectin- and M6PR+PSGL-1-conjugated, caspase-3 siRNA-loaded liposomes were intravenously injected into the experimental mice. At 24 h after the plasma alanine aminotransferase (ALT) levels were analyzed (see FIG. 21). These results suggested that these protein-conjugated liposomes are not only able to target to injured tissues, but also are able to carry RNA to cure target tissues (see FIG. 21).

In thioacetamide (TAA) hepatitis mouse model, the M6PR, M6PR+P-selectin-, M6PR+E-selectin- and M6PR+PSGL-1-conjugated, antiapoptotic Bcl-xL-derived BH4 motif loaded liposomes were intravenously injected into the experimental mice. At 24 h after the plasma alanine aminotransferase (ALT) levels were analyzed (see FIG. 22).

In thioacetamide (TAA) hepatitis mouse model, the M6PR+galectin 3, M6PR+P-selectin, Siglec 2+P-selectin and Siglec 2+galectin 3-conjugated caspase 3 inhibitor-loaded liposomes were intravenously injected into the experimental mice. At 24 h after the plasma alanine aminotransferase (ALT) levels were analyzed (see FIG. 23).

Example 7

The Targeting of CD34+ Cells with the Protein-Conjugated Liposome of the Invention to the Injury Site and the Synergistic Effect of Protein-Conjugated Liposome on CD34+ Cells-Mediated Rescue Fluorescence (calcein red) labeled mouse CD34$^+$ stem cells (1×10$^7$ cells/mouse) were intravenously injected into the experimental mice accompanied with M6PR and M6PR+P-sel conjugated liposome/MVs ($2.5 \times 10^9$ MVs/mouse). The fluorescence levels were determined using an IVIS system (see FIG. 24).

In thioacetamide (TAA) hepatitis mouse model, the mouse CD34$^+$ stem cells ($1 \times 10^7$ cells/mouse) were intravenously injected into the experimental mice accompanied with M6PR, M6PR+P-selectin-, M6PR+E-selectin- and M6PR+PSGL-1-conjugated liposomes/MVs ($2.5 \times 10^9$ MVs/mouse). At 24 h after the plasma alanine aminotransferase (ALT) levels were analyzed (see FIG. 25).

Example 8

The Targeting of an Anticancer Drug or a Cell Suppressing Agent to Cancer Cells with Protein-Conjugated Liposome of the Invention The mice were subcutaneously injected with B16-F10 melanoma cell ($1*10^6$ cell/mice) to groin site. At the third day and eighth day, MVs (containingt mitomycin C, 0.2 µg) and MVs (containing cisplatin: 2 µg) were injected to the orbital sinus of the mice, respectively. The mice were sacrificed at the twelfth day to take out the tumors. The size and weight of the tumors were determined (see FIGS. 26(a) and (b)). As shown in FIG. 26, MVs can carry the anticancer drug to the tumors and deliver the drug into the tumors to inhibit or alleviate tumor growth and reduce tumor size.

Figure 27:
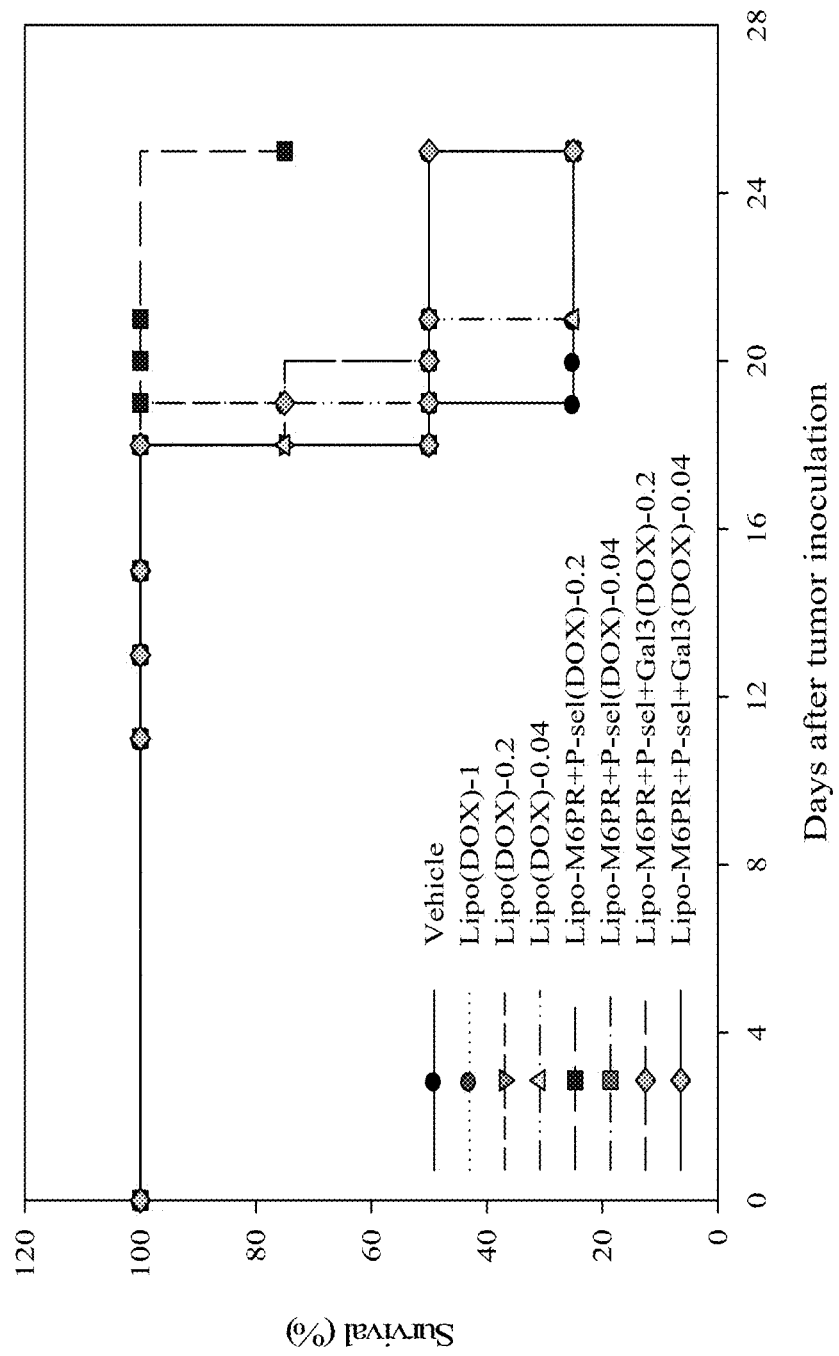

According to the above-mentioned method, protein-conjugated engineered liposomes (containing doxorubicin) were used as carrier carrying the anticancer drug. As shown in FIG. 27, protein-conjugated engineered liposomes (containing doxorubicin) can inhibit tmopr growth rate (see FIG. 27(a)) and that also can reduce the mortality rate of the mice (FIG. 27(b)).

Example 9

The Targeting of a Drug to Adipose Tissue with the Protein-Conjugated Liposome of the Invention The mice with high fat diet were injected with the control Igs or anti-fat antibody (75 µg/mice) to orbital sinus at 0 and 48 hours, respectively. At 6 hours, 24 hours, 54 hours and 72 hours, MVs (containing mitomycin C, 0.2 µg) and MVs (containing cisplatin: 2 µg) were injected to the orbital sinus of the mice, respectively. The weights of the mice were determined and the results are shown in FIG. 28. The results show that MVs (containing mitomycin C, 0.2 µg) can reduce the weight increasing rate of the mice.

Figure 29B:
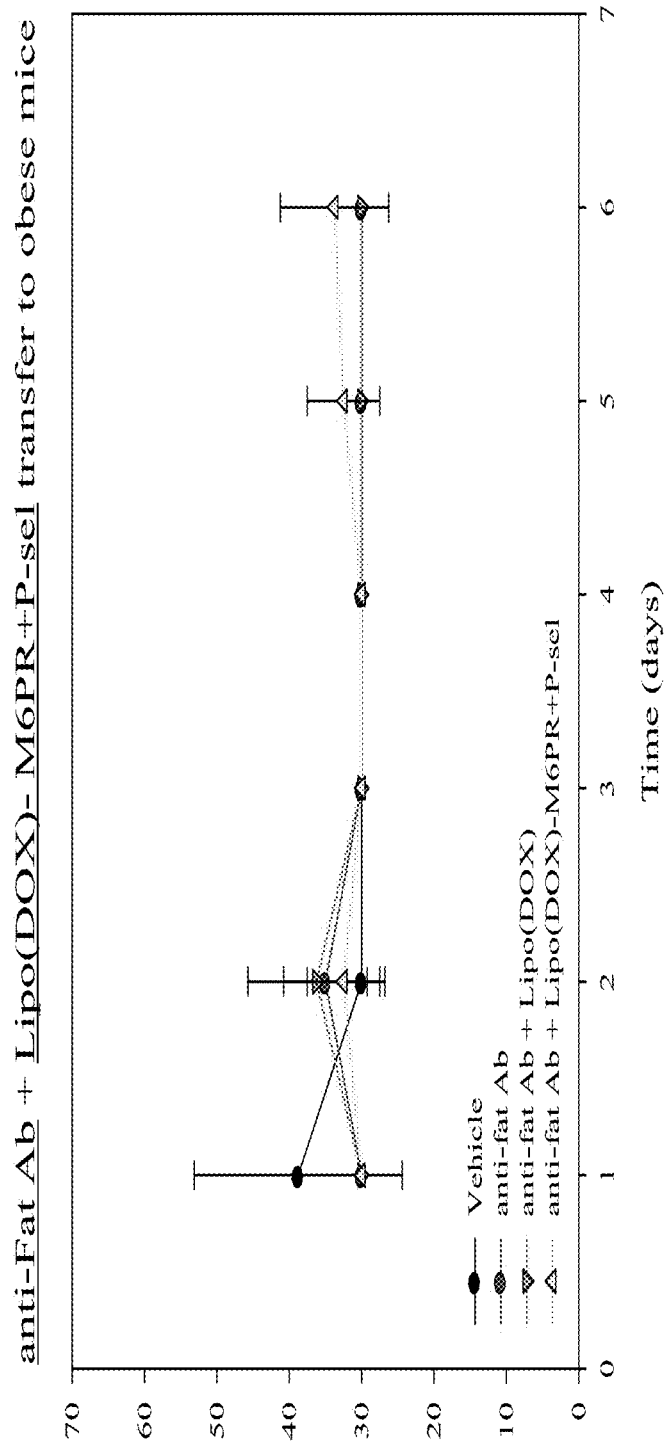

According to the above-mentioned method, the protein-conjugated engineered liposomes (containing doxorubicin) was used in the assay. As shown in FIG. 29, the protein-conjugated engineered liposomes (containing doxorubicin) can reduce the weight increasing rate of the mice (FIG. 29(a)). In addition, the anti-fat antibody or liposomes (containing doxorubicin) will not cause an increase in liver function index (FIG. 29(b)).

Example 10

The Protein-Conjugated Liposome of the Invention Only Mediate Rescue on Injury Tissues without Loaded with Additional Drugs/Materials Plasma MVs express P-selectin relative higher levels of surface P-selectin as compared to the serum and cell (C6/36)-derived MVs. Analyzed by flow cytometry (see FIG. 30).

In thioacetamide (TAA) hepatitis mouse model, the plasma, serum and cell (C6/36)-derived MVs ($2.5 \times 10^9$ MVs/mouse) were intravenously injected into the experimental mice. At 24 h after the plasma alanine aminotransferase (ALT) levels were analyzed (see FIG. 31).

In thioacetamide (TAA) hepatitis mouse model, the mouse CD34$^+$ stem cells ($1 \times 10^7$ cells/mouse) were intravenously injected into the experimental mice accompanied with plasma, serum and cell (C6/36)-derived MVs ($2.5 \times 10^9$ MVs/mouse). At 24 h after the plasma alanine aminotransferase (ALT) levels were analyzed (see FIG. 32).

We claim:

1. A protein-conjugated vesicle, comprising one or more lectins or a fragment thereof expressed or conjugated to the surface of the vesicle and optionally an agent separate from the lectin or fragment thereof and encapsulated within said vesicle or attached to the outer surface of said vesicle; wherein said one or more lectins or fragment thereof is selected from cation-dependent mannose-6-phosphate receptor (M6PR), P-selectin, E-selectin, L-selectin, P-selectin-ligand-1 (PSGL-1), CD22, CD206, galectin 3, annexin V, CD31, integrin αLβ2, VE-cadherin, CD44, CD300a, CD47, thrombospondin 1 (TSP1), CD36 and a fragment thereof.

2. The vesicle of claim 1, wherein the vesicle is a liposome or a micelle.

3. The vesicle of claim 1, wherein the vesicle is artificially engineered.

4. The vesicle of claim 1, wherein said vesicle further comprises one or more lectins or a fragment thereof is selected from the group consisting of: CD300a, CD47, thrombospondin 1 (TSP1), CD36, Toll like receptor 4 (TLR4), and a fragment thereof.

5. The vesicle of claim 1, which comprises M6PR in combination with P-selectin, E-selectin, PSGL-1 or galectin 3.

6. The vesicle of claim 1, which comprises Siglec 2 in combination with P-selectin, galectin 3 or CD31.

7. The vesicle of claim 1, which comprises P-selectin or M6PR in combination with TLR4, galectin 3, CLEC2, Integrin αLβ2 or CD31.

8. The vesicle of claim 1, wherein the agent is a diagnostic contrast agent, a cell survival enhancing agent, a cell survival suppressing agent, a cell component, an organelle, a cell, a cytotoxic agent, an antitumor drug, a toxin or an antibody a lipid, a protein, DNA, RNA, a therapeutic agent or a nanomaterial.

9. The vesicle of claim 1, wherein the vesicle is cell-derived.

10. A pharmaceutical composition comprising a vesicle of claim 1 and a pharmaceutically acceptable carrier.

11. A pharmaceutical composition comprising the vesicle of claim 1, and antagonists to the one or more lectins or a fragment thereof.

12. The composition of claim 11, wherein the antagonists to the one or more lectins or a fragment thereof are soluble forms of the lectins or fragments thereof, corresponding ligands to the lectins or fragments thereof, or antibodies to the lectins or fragments thereof.

13. The composition of claim 11, wherein said antagonists to the one or more lectins or a fragment thereof reduce the vesicle-targeting to autophagic and/or apoptotic cells and autophagic and/or apoptotic cells-containing tissues.

14. A method for delivery of an agent to an autophagic and/or apoptotic cell and a tissue containing the cell, comprising administering a protein-conjugated vesicle of claim 1 to a subject.

15. The method of claim 14, wherein before administration of the vesicle, the method additionally comprises a step of administering an autophagic and/or apoptotic-inducing agent to a cell or a target tissue.

16. The method of claim 14, wherein the delivery of an agent, a diagnostic agent or a therapeutic agent with the vesicle of claim 1 to autophagic cells is directed to a disease associated with autophagy deregulation.

17. The method of claim 16, wherein the disease associated with autophagy deregulation is trauma, exposure to chemical and physical toxic factors, genetic disease, age-related disease, cardiovascular disease, infectious disease, neoplastic disease, neurodegenerative disease, metabolic disease, aging, obesity, cancer, neurodegeneration induced by β-amyloid or α-synuclein or toxicity, myodegenerative conditions, or chronic lung inflammation caused by cystic fibrosis.

18. The method of claim 14, wherein the delivery of an agent, a diagnostic agent or a therapeutic agent with the vesicle of claim 1 to apoptotic cells is directed to a disease associated with apoptosis alteration.

19. The method of claim 18, wherein the disease associated with apoptosis alteration is trauma, exposure to chemical and physical toxic factors, genetic disease, age-related disease, age-related disease, cardiovascular disease, infectious disease, neoplastic disease, neurodegenerative disease, metabolic disease, aging, obesity, cancer, neurodegeneration induced by β-amyloid or α-synuclein or toxicity, myodegenerative conditions, or chronic lung inflammation caused by cystic fibrosis, or autoimmune disease.

20. The method of claim 19, wherein the neurodegenerative disorder is Alzheimer's disease, Parkinson's disease, Huntington's disease, Amyotrophic Lateral Sclerosis or stroke, the cardiovascular disorder is ischemia, heart failure or infectious disease and the autoimmune disease is systemic lupus erythematosus, autoimmune lymphoproliferative syndrome, rheumatoid arthritis or thyroiditis.

* * * * *